(12) United States Patent
Zhang et al.

(10) Patent No.: US 9,530,060 B2
(45) Date of Patent: Dec. 27, 2016

(54) SYSTEM AND METHOD FOR BUILDING AUTOMATION USING VIDEO CONTENT ANALYSIS WITH DEPTH SENSING

(71) Applicant: Avigilon Fortress Corporation, Vancouver (CA)

(72) Inventors: Zhong Zhang, Great Falls, VA (US); Gary W. Myers, Aldie, VA (US); Peter L. Venetianer, McLean, VA (US)

(73) Assignee: AVIGILON FORTRESS CORPORATION, Vancouver, British Columbia (CA)

( * ) Notice: Subject to any disclaimer, the term of this patent is extended or adjusted under 35 U.S.C. 154(b) by 79 days.

(21) Appl. No.: 13/744,264

(22) Filed: Jan. 17, 2013

(65) Prior Publication Data
US 2013/0182905 A1    Jul. 18, 2013

Related U.S. Application Data

(60) Provisional application No. 61/587,186, filed on Jan. 17, 2012.

(51) Int. Cl.
*G06K 9/00* (2006.01)
*H04N 7/18* (2006.01)
(Continued)

(52) U.S. Cl.
CPC ......... *G06K 9/00718* (2013.01); *A61B 5/0013* (2013.01); *A61B 5/0046* (2013.01);
(Continued)

(58) Field of Classification Search
CPC .............. G08B 13/19608; G08B 13/08; G08B 13/19602; G06K 9/00221; G06K 9/00771; G06K 9/3216; G06K 9/00718; G06K 9/00369; G06T 7/2006; G06T 7/2033; H04N 7/18; A61B 5/0013; A61B 5/0046; A61B 5/0077; A61B 5/1072; A61B 5/1073; A61B 5/1113; A61B 5/1116; A61B 5/1176; A61B 5/7282; A61B 5/746; A61B 5/1079; A61B 5/1117; A61B 5/1128
(Continued)

(56) References Cited

U.S. PATENT DOCUMENTS 5,544,649 A    8/1996   David et al.
5,553,609 A    9/1996   Chen et al.
(Continued)

FOREIGN PATENT DOCUMENTS

KR        100234196 B1     12/1999
WO       WO 2012/037157 A2   3/2012

OTHER PUBLICATIONS

Potapova et al, "Calculation of Attention Points Using 3D Cues". Automation and Control Institute Vienna University of Technology.
(Continued)

*Primary Examiner* — Vu Le
*Assistant Examiner* — Kenny Cese
(74) *Attorney, Agent, or Firm* — Muir Patent Law, PLLC

(57) ABSTRACT

A method and system for monitoring buildings (including houses and office buildings) by performing video content analysis based on two-dimensional image data and depth data are disclosed. Occupation and use of such buildings may be monitored with higher accuracy to provide higher energy efficiency usage, to control operation of components therein, and/or provide better security. Height data may be obtained from depth data to provide greater reliability in object detection, object classification and/or event detection.

26 Claims, 20 Drawing Sheets

(51) Int. Cl.
- A61B 5/00 (2006.01)
- A61B 5/107 (2006.01)
- A61B 5/11 (2006.01)
- A61B 5/117 (2016.01)
- G08B 13/196 (2006.01)
- G08B 21/04 (2006.01)
- G06T 7/00 (2006.01)
- G06T 7/20 (2006.01)

(52) U.S. Cl.
CPC .......... *A61B 5/0077* (2013.01); *A61B 5/1072* (2013.01); *A61B 5/1073* (2013.01); *A61B 5/1079* (2013.01); *A61B 5/1113* (2013.01); *A61B 5/1116* (2013.01); *A61B 5/1117* (2013.01); *A61B 5/1128* (2013.01); *A61B 5/1176* (2013.01); *A61B 5/7282* (2013.01); *A61B 5/746* (2013.01); *G06K 9/00369* (2013.01); *G06K 9/00771* (2013.01); *G06T 7/0042* (2013.01); *G06T 7/0071* (2013.01); *G06T 7/2033* (2013.01); *G08B 13/19615* (2013.01); *G08B 21/043* (2013.01); *G08B 21/0476* (2013.01); *H04N 7/18* (2013.01); *H04N 7/181* (2013.01); *G06K 2009/00738* (2013.01); *G06T 2207/10016* (2013.01); *G06T 2207/30196* (2013.01); *G06T 2207/30232* (2013.01)

(58) Field of Classification Search
USPC ........................................................ 382/103
See application file for complete search history.

(56) References Cited

U.S. PATENT DOCUMENTS

| | | | |
|---|---|---|---|
| 6,792,319 B1* | 9/2004 | Bilger | 700/13 |
| 7,516,888 B1 | 4/2009 | Kundu et al. | |
| 7,801,330 B2 | 9/2010 | Zhang et al. | |
| 7,825,954 B2 | 11/2010 | Zhang et al. | |
| 7,831,087 B2 | 11/2010 | Harville | |
| 7,868,912 B2 | 1/2011 | Venetianer et al. | |
| 7,932,923 B2 | 4/2011 | Lipton et al. | |
| 8,233,660 B2 | 7/2012 | Fritsch et al. | |
| 8,238,607 B2 | 8/2012 | Wang et al. | |
| 8,320,621 B2 | 11/2012 | McEldowney | |
| 2003/0034971 A1 | 2/2003 | Fujiwara et al. | |
| 2004/0153671 A1* | 8/2004 | Schuyler et al. | 713/201 |
| 2005/0201612 A1 | 9/2005 | Park et al. | |
| 2007/0070190 A1 | 3/2007 | Yin et al. | |
| 2007/0127774 A1* | 6/2007 | Zhang et al. | 382/103 |
| 2008/0021731 A1 | 1/2008 | Rodgers | |
| 2009/0063307 A1 | 3/2009 | Groenovelt et al. | |
| 2009/0080711 A1 | 3/2009 | Yokoi | |
| 2009/0281392 A1 | 11/2009 | Brown | |
| 2010/0197393 A1 | 8/2010 | Geiss | |
| 2010/0199228 A1 | 8/2010 | Latta et al. | |
| 2011/0080336 A1 | 4/2011 | Leyvand et al. | |
| 2011/0134109 A1 | 6/2011 | Izumi | |
| 2011/0143779 A1 | 6/2011 | Rowe et al. | |
| 2011/0200229 A1 | 8/2011 | Tuzel et al. | |
| 2011/0285910 A1 | 11/2011 | Bamji et al. | |
| 2012/0020518 A1* | 1/2012 | Taguchi | 382/103 |
| 2012/0025989 A1 | 2/2012 | Cuddihy et al. | |
| 2012/0026289 A1* | 2/2012 | Suenaga | H04N 13/0018 348/44 |
| 2012/0026308 A1 | 2/2012 | Johnson et al. | |
| 2012/0075464 A1 | 3/2012 | Derenne et al. | |
| 2012/0087572 A1* | 4/2012 | Dedeoglu | G06K 9/00771 382/154 |
| 2012/0087573 A1 | 4/2012 | Sharma et al. | |
| 2012/0140068 A1 | 6/2012 | Monroe et al. | |
| 2012/0293635 A1 | 11/2012 | Sharma et al. | |
| 2012/0314905 A1 | 12/2012 | Wang et al. | |
| 2013/0041290 A1 | 2/2013 | Kording et al. | |
| 2013/0073093 A1* | 3/2013 | Songkakul | 700/276 |
| 2013/0182114 A1 | 7/2013 | Zhang et al. | |
| 2013/0182904 A1 | 7/2013 | Zhang et al. | |
| 2013/0184592 A1 | 7/2013 | Venetianer et al. | |
| 2013/0184887 A1 | 7/2013 | Ainsley et al. | |

OTHER PUBLICATIONS

Steinbrücker et al, "Real-Time Visual Odometry from Dense RGB-D Images". Department of Computer Science, Technical University of Munich, Germany.

* cited by examiner

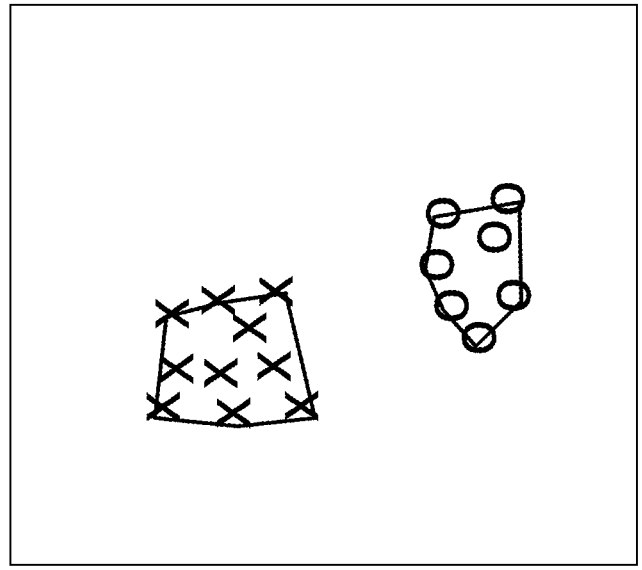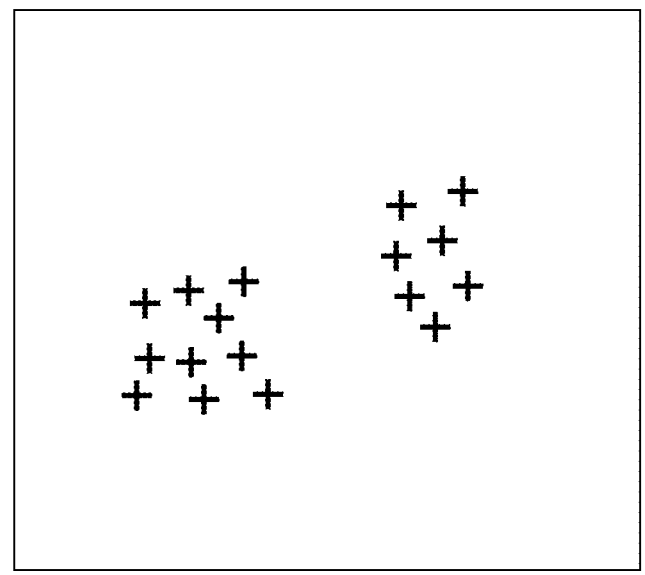

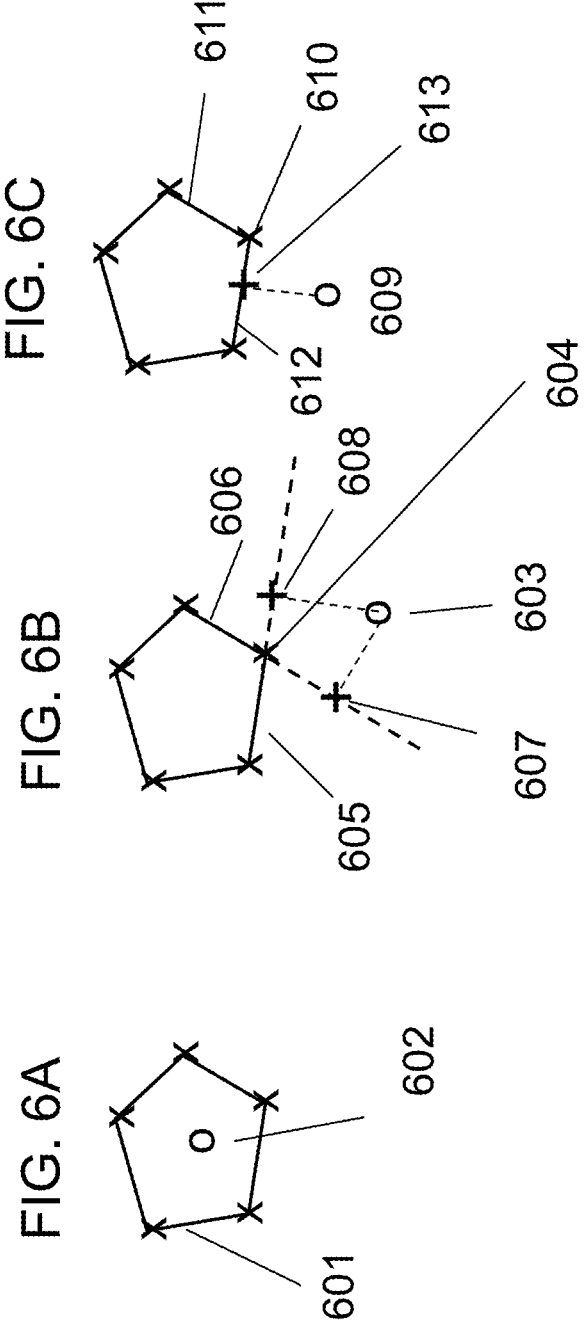

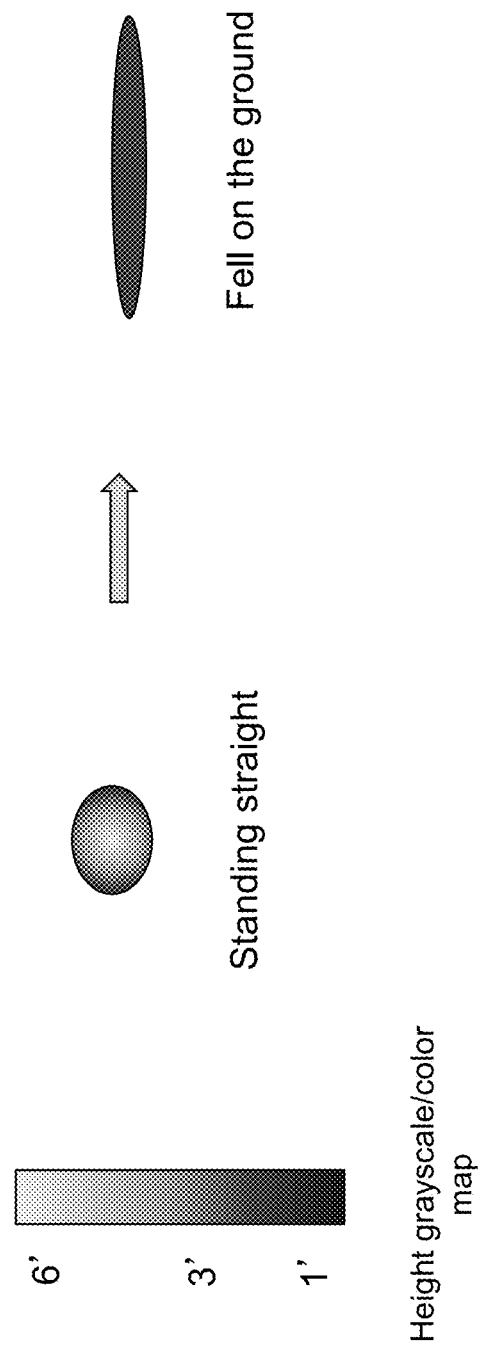

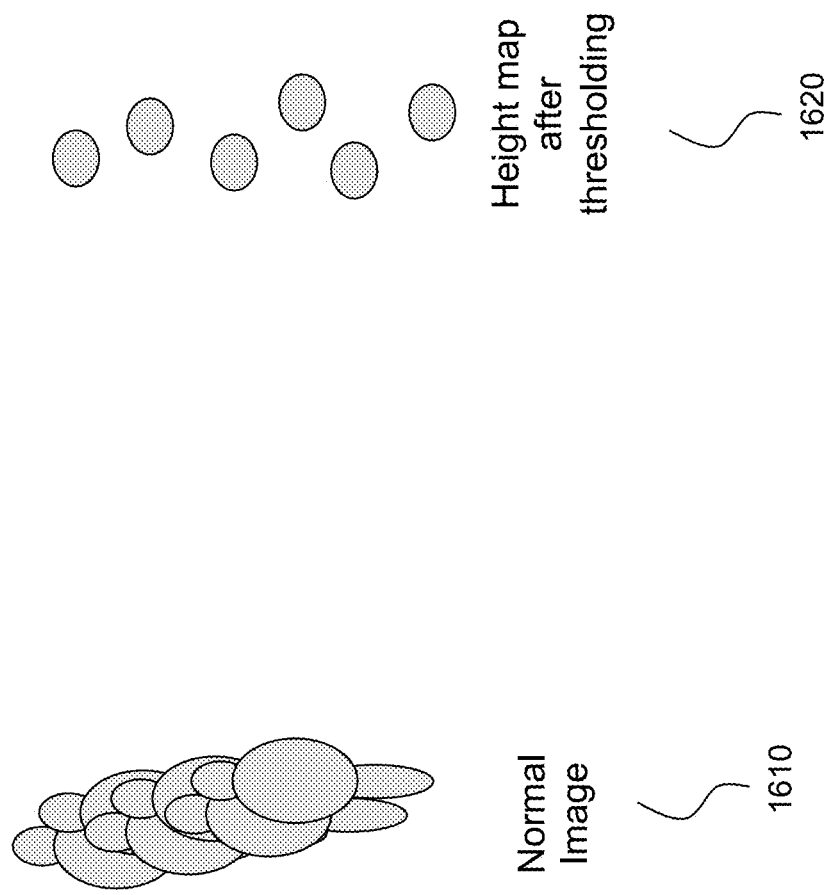

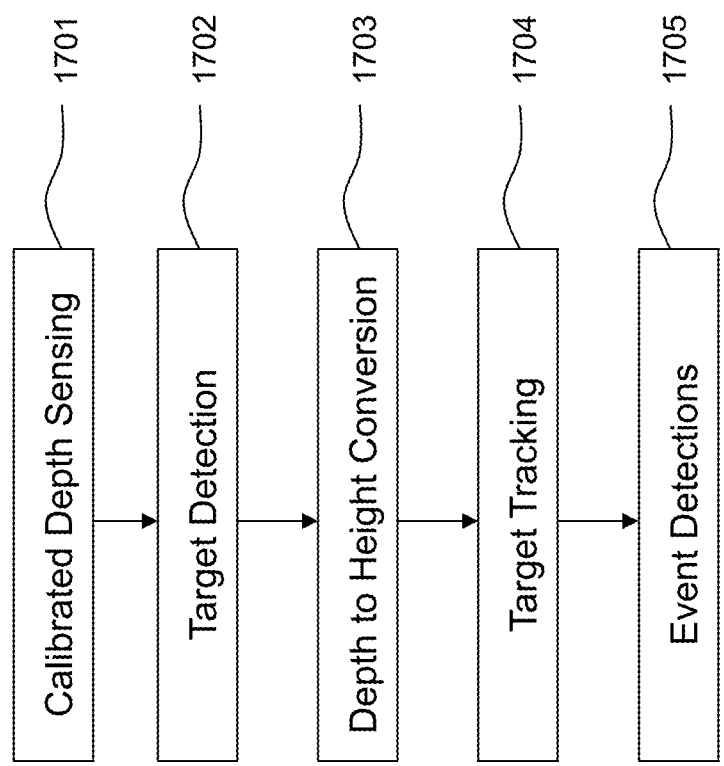

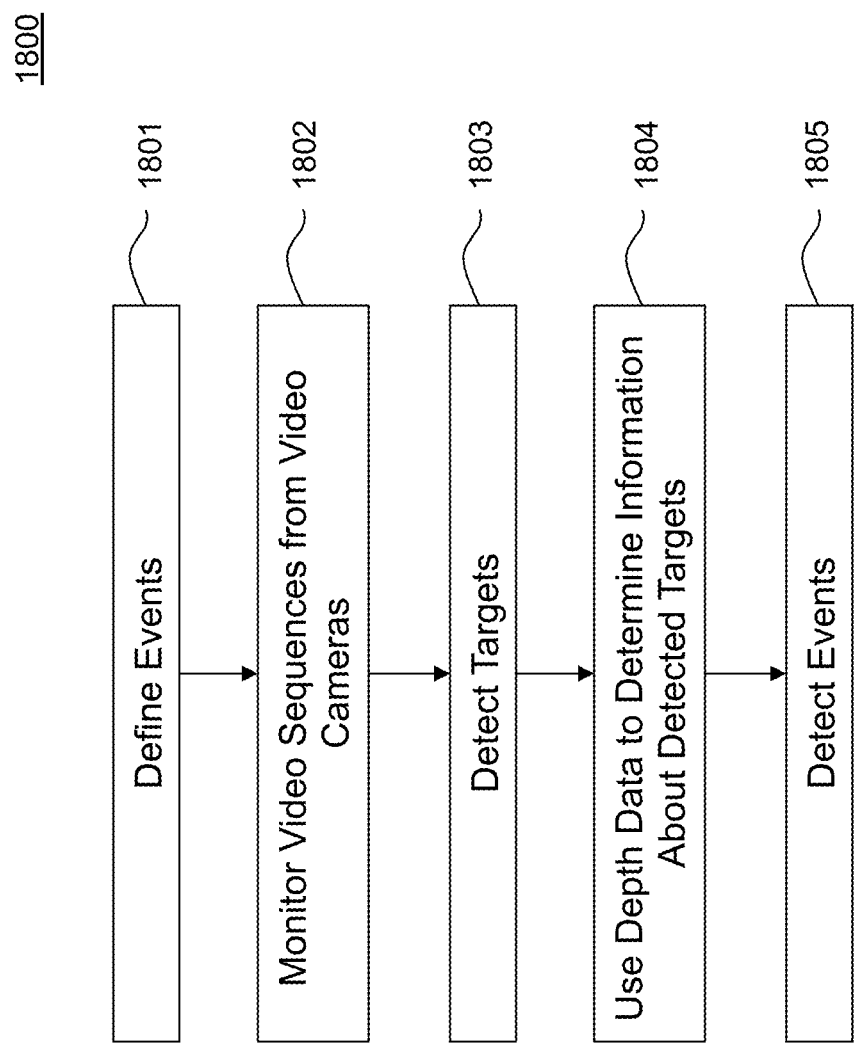

SYSTEM AND METHOD FOR BUILDING AUTOMATION USING VIDEO CONTENT ANALYSIS WITH DEPTH SENSING

CROSS-REFERENCE TO RELATED APPLICATION

This application claims the benefit of priority to U.S. Provisional Patent Application No. 61/587,186, filed Jan. 17, 2012, the contents of which are incorporated herein by reference in their entirety.

BACKGROUND

1. Field

This disclosure relates to a system for performing video content analysis (VCA) using depth information to assist monitoring building occupancy and/or usage.

2. Background

Use of video to monitor building occupancy and usage by the occupants can be very helpful. Video can be reviewed in real time, or later after storage, for a variety of purposes, such as security, energy efficiency and convenience to the building occupant. However, monitoring videos by a person may not be practicable for many applications. To assist in reviewing video, video content analysis systems have been designed. In a video content analysis (VCA) system, video streams are automatically analyzed to identify and classify objects, and to determine physical and temporal attributes of the objects. As a result, a log of analytics data may be stored. The analytics data may be used to determine events that occur in real time or at a later time, to aid in searching for objects or detected events, and for other purposes. An example of a VCA system is described in U.S. Pat. No. 7,932,923, issued to Lipton et al. on Apr. 26, 2011 (the '923 patent) and as well in U.S. Pat. No. 7,868,912 issued to Venetianer et al. on Mar. 11, 2011, the contents of each of which are incorporated herein by reference in their entirety.

Some existing systems use RGB (red green blue) or other image sensors that sense images in a two-dimensional manner and perform analysis of those images to perform object and event detection. However, identifying objects and related actions using RGB image sensors may be prone to error. For example, a VCA system may make a determination that an object is a human based on an analysis of the shape of the detected object (e.g., the detected object has a certain shape, such as a particular size relationship of a detected torso, head and arm/leg appendages). However, such analysis to determine that an object is a human may equally apply to the shadow of a human in a building. (As used in this disclosure, a "building" refers to both commercial buildings (e.g., office buildings, warehouses, etc.) as well as residential houses and other buildings). If the VCA system is interested in determining occupancy of a building or usages of or within the building, inaccurate detection of people and/or their actions may result in undesirable actions or inactions. For example, if a system is designed to turn off lights when no one in a certain location of a building is detected, an inaccurate assessment of an object as not a person may result in lights being turned off at the location even when a person is present, possibly creating a dangerous situation. Conversely, if a system is designed to provide energy efficient heating and cooling if a low number of people are detected to be present, inaccurate detection of shadows and/or reflections as people may cause the system to provide inefficient heating and cooling, creating waste and higher usage costs of the building.

The embodiments described here address some of these problems of existing building monitoring systems, and provide use of depth and/or height data to assist in monitoring a buildings and their usage. As a result, a more accurate system and method for detecting and tracking building occupants and their actions may be achieved.

SUMMARY

The disclosed embodiments provide a method and system for monitoring buildings by analyzing video and performing video content analysis using depth data.

In some examples, a method of monitoring a building comprises taking a video within a location in the building with a video sensor, the video comprising a plurality of frames, each frame including image data; for each frame, receiving depth data associated with the image data, the depth data corresponding to one or more distances from the video sensor to features represented by the image data; analyzing the image data and depth data to detect and classify one or more objects depicted in the video, classification of the one or more objects comprising determining whether at least some of the one or more objects are people; counting a number of people based on the analyzing of the image data and the depth data; and controlling a system of the building in response to the number of people counted. A system is also disclosed for performing one or more of the various exemplary methods described herein.

BRIEF DESCRIPTION OF THE DRAWINGS

Example embodiments will be more clearly understood from the following detailed description taken in conjunction with the accompanying drawings. The figures represent non-limiting example embodiments as described herein.

FIGS. 5A-5B show examples of two separate groups of pixels in a Z-plane, according to certain exemplary embodiments.

FIGS. 6A-6C show exemplary methods of computing the distance between a pixel and convex null, according to certain embodiments.

FIG. 15 shows another example of an application of a combined calibration and depth detection system such as described in FIGS. 1-12, according to one embodiment.

FIG. 16 shows another example of an application of a combined calibration and depth detection system such as described in FIGS. 1-12, according to one embodiment.

FIG. 17 depicts an exemplary method of performing video content analysis using depth sensing, according to certain exemplary embodiments.

FIG. 18 depicts an exemplary method for monitoring a building using a video content analysis system that uses depth sensing, according to certain exemplary embodiments.

DETAILED DESCRIPTION

Figure 1:
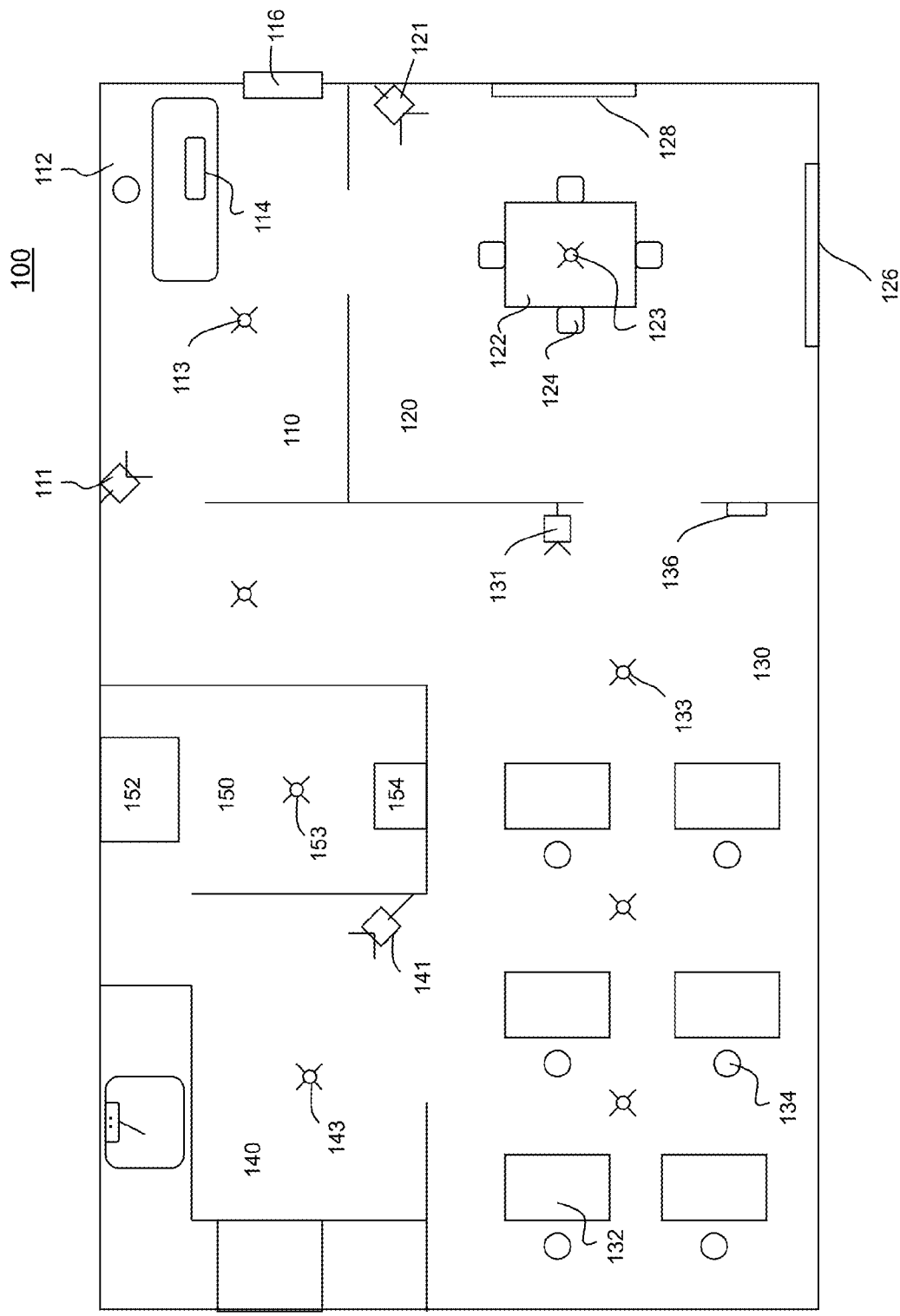
FIG. 1 illustrates an exemplary implementation of systems and methods at a floor of a building according to certain embodiments.

The present disclosure will be described more fully hereinafter with reference to the accompanying drawings, in which various embodiments are shown. The invention may, however, be embodied in many different forms and should not be construed as limited to the embodiments set forth herein. In the drawings, like numbers refer to like elements throughout.

It will be understood that when an element is referred to as being "connected" or "coupled" to or "in communication with" another element, it can be directly connected or coupled to or in communication with the other element or intervening elements may be present. In contrast, when an element is referred to as being "directly connected" or "directly coupled" or "in direct communication with" another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. Unless indicated otherwise, these terms are only used to distinguish one element from another. For example, a first signal could be termed a second signal, and, similarly, a second signal could be termed a first signal without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

This disclosure includes particular terminology and descriptions that relate to video surveillance and analysis. The descriptions are intended to provide a framework for certain terms and concepts, and are not intended to limit the scope of this disclosure unless explicitly stated.

VCA systems may use cameras that are calibrated in order to detect and identify objects. For example, rather than simply detecting an object based on its relative dimensions, which can represent, for example, a shape of an automobile or a shape of a human being, calibrated VCA systems are able to detect a shape of an object as well as its real-world size. As a result, the system can more accurately detect certain objects. For example, in a non-calibrated system, a VCA system for counting a number of people that appear in a frame of a video stream may count the shapes of both actual people, and of miniature dolls in the frame as people. To avoid this sort of error, VCA systems can be calibrated to provide scale and determine the actual sizes (e.g., actual height and width dimensions) of objects, which improves analysis accuracy.

VCA systems may use cameras that are calibrated in order to detect and identify objects. For example, rather than simply detecting an object based on its relative dimensions, which can represent, for example, a shape of an automobile or a shape of a human being, calibrated VCA systems are able to detect a shape of an object as well as its real-world size. As a result, the system can more accurately detect certain objects. For example, in a non-calibrated system, a VCA system for counting a number of people that appear in a frame of a video stream may count the shapes of both actual people, and of miniature dolls in the frame as people. To avoid this sort of error, VCA systems can be calibrated to provide scale and determine the actual sizes (e.g., actual height and width dimensions) of objects, which improves analysis accuracy.

FIG. 1 illustrates an exemplary implementation of systems and methods according to the embodiments described herein. In this example, FIG. 1 illustrates a floor of an office building 100, but the invention is not limited thereto and can be applied to other types of buildings, including warehouses, apartment building, stand alone family residences, etc. In FIG. 1, the floor of an office building 100 includes a reception area 110, a conference room 120, a workspace area 130, a lunch room 140 and a utility closet 150.

The reception area 110 includes a reception desk 112 with a networked computer 114. The floor of the office building may be entered or exited via door 116 at the reception area 110.

The conference room 120 includes a conference table 122 with chairs 124. The conference room may include a television or a display for a projector (e.g., for presentations), shown as 126 in FIG. 1. The conference room may also include a window with adjustable blinds 128.

The workspace area includes a plurality of desks 132 and chairs 134. Cubicle type wall dividers (not shown) may divide the workspace area to provide workers some privacy. The work space area 130 may include a thermostat 136.

Utility closet 150 may include an HVAC (heating, ventilating and air conditioning system) 152 and a server 154. Server 154 may be networked with computer 114, other on-site or off-site computers (not shown) and devices within the building.

Some or all of the rooms may be provided with a video camera and a depth sensor. Here, video cameras/depth sensors 111, 121, 131, 141 have been respectively installed in the reception area 110, the conference room 120, the workspace area 130 and the lunch room 140. It may be desirable to install video camera/depth sensors as well in the utility closet 150 and the hallway connecting the workspace area 130 and the reception area 110. Each video camera takes and records two-dimensional 2D image data to obtain a video image of the area of the floor of the office building 100 being recorded. Each video camera is also associated with a depth sensor that measures the distance of objects from the depth sensor and video camera. Exemplary details of the depth sensors, video camera and processing are discussed in further detail below.

Lights 113, 123, 133, 143 and 153 are also provided in each of the rooms and may be overhead lights mounted in a ceiling. Light switches in an electrical lighting circuit may control the on/off state of the corresponding lights in the lighting circuit. For example, each room of the floor of the office building may have a set of one or more lights controlled by a corresponding electrical lighting circuit and one or more switches.

Each of the video cameras/depth sensors 111, 121, 131, 141 may be networked or otherwise in communication (e.g., hard wired or wirelessly) with server 154. Each video camera may include a processor to perform video content analysis of the corresponding video images captured. The content analysis may analyze the two dimensional video image data with the depth information provided by the depth sensor associated with the video camera, and may also analyze the two dimensional video image data alone. On camera processors of each video camera may perform such content analysis to generate video primitives, also referred to herein as metadata, and stream the video primitives/metadata to the server 154. The video primitives/metadata may represent detected objects, detected classification and/or characteristics of the detected objects and/or actions and/or events (e.g., of the detected objects) detected in the corresponding video. The video primitives, or metadata, may be associated with each frame of the video sequence. By way of example, see U.S. Pat. No. 7,868,912 issued to Venetianer et al. and U.S. Pat. No. 7,932,923 issued to Lipton et al. for exemplary details of video primitive (or metadata) generation and downstream processing (which may be real time processing or later processing) to obtain information from the video, such as event detection, using the generated video primitives. Depth data associated with the video image data may be provided to server 154 as metadata along with other metadata. Alternatively and/or in addition, height data derived from the depth data (e.g., from on camera processing) may be provided to server 154 as metadata along with other metadata. The depth metadata and/or height metadata may be associated with detected objects and may include depth and/or height of multiple elements of the detected object. The depth and/or height data and other metadata obtained from on camera processing of the video image data of the corresponding video camera may be streamed to server 154.

Alternatively, the video camera/depth sensors 111, 121, 131, 141 may provide recorded video and associated depth data to the server 154 or another computer without processing. In this example, each camera may stream to server 154 or to another computer the video image data together with the depth data. Server 154 or the other computer may then process the video image data and depth data provided by the video cameras/depth sensors 111, 121, 131, 141. Such processing may also generate metadata derived from the video image data and depth metadata and/or height metadata as described previously.

The metadata may be processed to classify objects, and to detect actions and events without reprocessing the original video image data. Upon detecting an action/event of interest, the original video image data may be accessed by a user to verify the action/event detection or to review for other purposes.

Server 154 may be networked with or otherwise in communication with the electrical lighting circuits of each room 110, 120, 130, 140 and 150, receptionist computer 114, locking mechanism of door 110, television/display 126, blinds 128, thermostat 136, and HVAC system 152. For example, server 154 may be connected to operate a switch inserted into a lighting circuit to interrupt power flow within the lighting circuit to turn off lights, turn on lights and/or allow/disallow operation of lights by users. The server 154 may be connected to operate the locking mechanism of door 110 to lock or unlock the door 110. The server 154 may be connected to operate blinds 128 to open and close. The server 154 may be connected to receive temperature information from thermostat 136 and to control HVAC 152. HVAC 152 may be controlled by server 154 by setting a temperature of the thermostat 136, that in turn controls HVAC 152 based on the set temperature. Each of these connections of the server may be a hard wire connection to transmit or interrupt transmission of power to these devices, a wireless connection to communicate with a controller associated with the device to instruct the device controller to operate the device, and/or signal communication provided on electrical wiring providing power to the device.

The server 154 may be networked to receptionist computer 114, to computers external to the building (e.g., at a central monitoring station monitoring plurality of buildings), and/or may be connected to the internet or a telephone system to provide alerts. Alerts may be in the form of messages, such as e-mail messages or text messages to mobile phones. Alerts may have different levels to provide alerts of interest, warning alerts and emergency alerts, where the alert level may cause different processing by the receiving device. Although server 154 is shown to be located on site on the floor of the office building 100, it may be located at a different location, such as on a different level or outside the office building. For example, the server 154 may be in communication with video cameras/depth sensors and controlled devices within the building via a virtual private network that may employ the internet for communication.

In operation, video cameras/depth sensors 111, 121, 131, 141 generate two dimensional video image data and corresponding depth data providing depth information regarding features (such as objects) within the two dimensional video data. The video image data and depth data is analyzed in various ways to detect objects, classify or identify objects, and/or to determine actions and/or events of the detected objects. Such analysis may be performed by processors at each of the video cameras/depth sensors 111, 121, 131, 141, at the server, or by computers offsite (e.g., networked with the server to receive images and or video primitives representing characteristics detected within the video image data).

Based upon desired use of the system, the system may be configured to take many actions and provide various alerts. Actions may be performed automatically without approval, or automatically after approval (e.g., after receiving approval of a suggested action by sending an alert to an appropriate user and receiving a confirmation from the user to perform the action). Actions to be performed may depend on the action/event that is detected by the system. By way of example, upon detecting the absence of people in an area, lights within the area may be turned off. When detecting the presence of people in an area, lights within the area may be turned on. Upon detecting no or minor amounts of people (e.g., one person for the entire floor or house) within the entire location (or a heating/cooling zone of a location, such as an upper floor of a house that is separately heated/cooled), temperature settings for the HVAC 152 may be made energy efficient. Upon detecting enough people within the location (or heating/cooling zone), more comfortable temperature settings may be set (e.g., via thermostat 136) and the HVAC 152 operated accordingly. Detecting an amount of people may be made by counting people detected by each individual camera or made by tracking the entering and exiting of people through doorway 110 camera 111 to determine a total remaining amount of people (of course, other used entrances to the floor of the office building 100 would need to be similarly monitored and people count totals coordinated). Conference room 120 can be monitored to determine if it is in use, and reception computer 114 notified of the same to assist needless interruptions of the conference room users. Blinds 128 may be operated to be open and closed in response to determining conference room users are viewing the television/display 126.

Alerts may be sent to particular locations (e.g., the receptionist computer) or to particular individuals (e.g., the cell phone of the building manager). Alerts may be provided with a still image (or snapshot) of the video image or a short clip of the video image associated with the alert (e.g., video that was responsible for generating the alert). In response to receiving the alert, receivers of the alert may communicate with the server to receive live video (e.g., from the video camera responsible for generating the alert). The alert may include a link that when selected by a user automatically retrieves and displays related video (e.g., live video or previously recorded video related to the detected action/event). For example, selection of a hyperlink sent with the alert may connect the computer to a URL identifying an internet address of the appropriate video camera or video file. In response to receiving the alert, receivers of the alert may establish an audio connection to listen to the area of interest (e.g., at an area having the video camera responsible for generating the alert). The audio connection may allow the receiver of the alert to simply listen and/or have a conversation with anyone in such area of interest.

These system actions are exemplary and other uses of the system are discussed herein. In these uses, inaccurate detection of objects, inaccurate identification of objects and/or inaccurate detection of actions/events may result in a lack of a desired action or alert or, alternatively, undesired actions or alerts. For example, if a shadow or a reflection from a person standing near a doorway of a lighted area falls within a second unlighted area, the shadow may be detected as a person by a camera in the second area. The system may decide it is desirable to turn on the lights in the second area. Upon turning on the lights, the shadow may disappear or fade so as not to be detected as a person, causing the system to turn off the lights in the second area, causing the shadow to reappear and the cycle to repeat itself. Using depth information of features depicted in the video image to analyze the video image provides higher accuracy for many types of analyses to provide better decision making by the system for taking actions and/or sending alerts.

Figure 2:
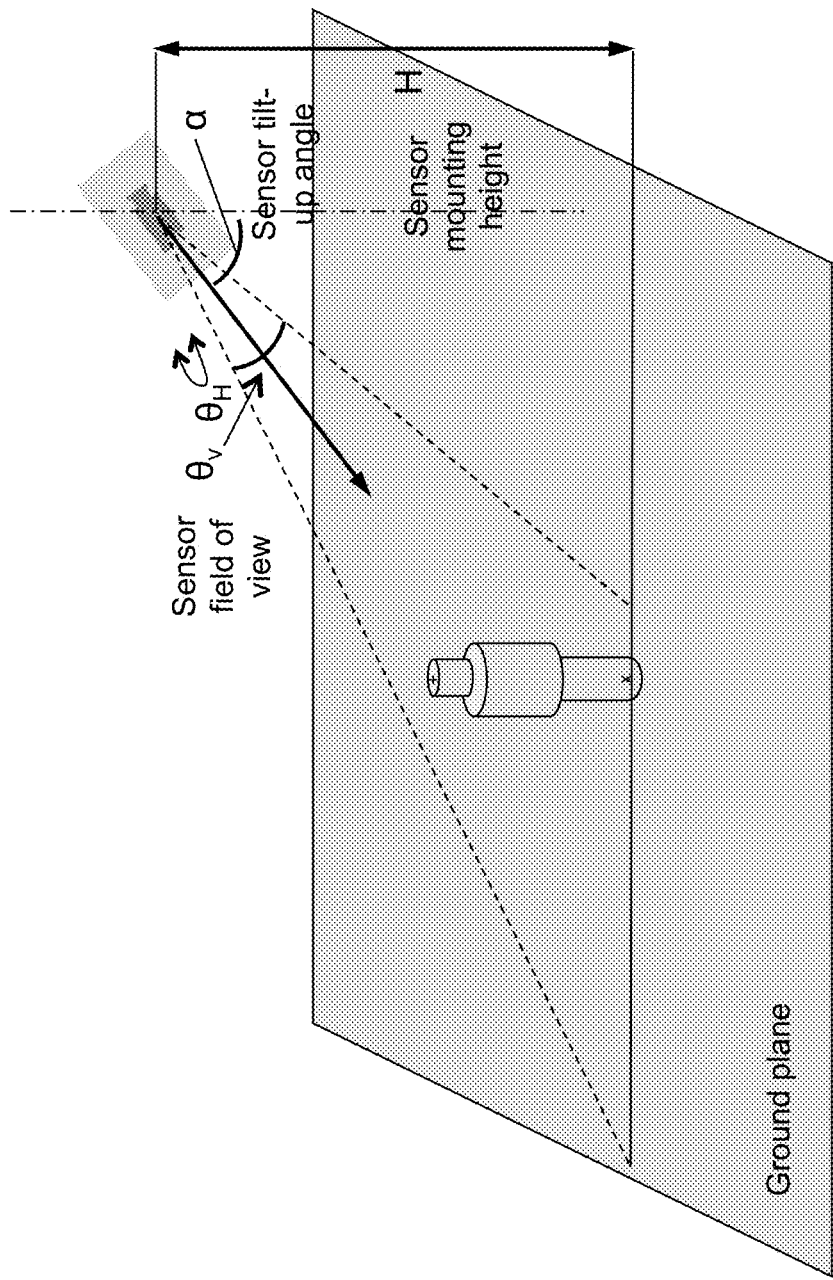
FIG. 2 shows a camera system that can be calibrated to assist in determining the scale and sizes of objects in the field of view, according to one exemplary embodiment.

As one example, FIG. 2 shows a camera system that can be calibrated to assist in determining the scale and sizes of objects in the field of view. To calibrate the camera system, parameters such as camera height (H), vertical and horizontal camera field of view angles ($\theta_H$, $\theta_V$), and camera tilt angle ($\alpha$) can be used. These parameters could be determined by direct measurement, camera specifications, or other calibration processes. For examples of calibration procedures, see the '923 patent, and see also U.S. Pat. No. 7,801,330, issued to Zhang et al. on Sep. 21, 2010, the contents of which are incorporated herein by reference in their entirety. Using these parameters and other information, such as detected outer boundaries of an object (e.g., a top and bottom of a person), the camera system can generally determine the real world size and shape of an object for identification purposes.

However, even a calibrated camera system can have some difficulties detecting real-world objects. For example, to determine an actual height of an object, such as a person, a calibrated system may search for the top of the object (e.g., the person's head) and the bottom of the object (e.g., the person's feet). However, part of a person's body, including the feet may be occluded by one or more objects, such as, for example, by another person, a chair, table, bed, cubicle wall, etc. In this case, the system may not be able to detect certain information about the person, such as the person's height. For example, if a second person is standing behind a first person, even if the system detects the second person, for example, based on an algorithm that detects human heads or faces, the system may not necessarily know the height of the second person. The second person may be taller than the first person and standing very close to the first person, or the second person may be shorter than the first person, but standing further away from the second person. In either case, however, the camera only sees the first person and the second person's head just above the first person.

Another example where a calibrated system may erroneously detect people or other objects is when shadows or reflections are involved. A calibrated camera system may see a shadow or reflection, and may determine, erroneously, that it is an actual person.

To remedy these problems, in one embodiment, a depth sensor is used together with the calibration information to help determine the real world height or size of an object. The depth sensor information can then be used to supplement, or verify information collected or determined by the calibrated camera system.

As opposed to inferring distance based on geometric equations, certain depth sensors determine the distance of objects from a sensor device by obtaining a direct measurement. For example, the measurement may be made using an infrared projector and a monochromatic CMOS sensor. An exemplary system for determining depth of objects in a three-dimensional space is described in U.S. Patent Application Publication No. 2010/0199228, to Latta et al., published on Aug. 5, 2010, the contents of which are incorporated herein by reference in their entirety. However, depth determination is not limited to the method disclosed in Latta et al., and depth can be determined based on a plurality of different sources, such as lidar, stereopsis, or structured light, for example.

In one embodiment, depth information can be used to supplement camera image information to determine the identity of certain objects. For example, in one embodiment, camera image information can be used to determine all potential human beings in a camera's field of view. For example, a calibrated camera system may be configured to detect objects that are not part of the background (e.g., moving objects) and that have a shape approximately the same shape as a human being. Depth sensor information can then be used to determine a real-world height or size of each object detected as a potential human being, and as a result, the number and location of actual human beings can be more accurately determined, for example, based on the potential human being objects that are above a certain height or that occupy a certain threshold volume. As an alternative, the depth sensor information can be used as a filter to count certain groups of people, for example, if only adults are desired to be counted.

Many methods have been proposed on using depth data to perform scene analysis. In U.S. Pat. No. 8,238,607 and U.S. Patent Application Publication No. 2012/0314905, for example, stereo videos are used to generate disparity map and depth map, and human detection and tracking are performed on the computed depth map. In U.S. Pat. No. 7,831,087, "Plan-View" images are generated from both depth data and non-depth data, and object detection is performed on the "Plan-view" images through "Plan-view" templates. In U.S. Pat. No. 8,320,621 and U.S. Patent Application Publication No. 2012/0197393, a new 3D imaging device RGBD sensor is introduced which can provide both RGB and Depth components for each pixel on the image. Humans and human body parts are detected and tracked on the depth map. In U.S. Patent Application No. 2005/0201612, stereo images are used to produce a height map, the human objects are detected by detecting heads using connect component analysis on the height map. In U.S. Patent Application Publication No. 2012/0293635, the above RGBD sensor is used to detect the head pose, and the head position and orientation are estimated by tracking head features points in 3D space.

Most of the prior art performs the object detection and tracking in the depth space or 3D space. This usually results in a lower resolution and lost details on the objects of interest. Further, the accuracy and quality of the depth data is usually not as good as those RGB image data, and methods of how to deal with the noise and incompleteness of the depth data in the scene analysis have not been well addressed. In addition, processing for object detection and tracking using 3D space data for a whole scene can be computationally complex or even prohibitive. In the present application, a way to use aligned depth data to assist in object detection/tracking under the existing non-depth sensor framework is proposed. The approach is based on the existing RGB image sensor based framework, and uses additional depth information to solve or alleviate certain existing problems. The object detection and tracking is still performed on the traditional non-depth 2D image space, and the depth data is used to provide physical location and size information on objects of interest to help the object detection, segmentation, classification and tracking processes.

Figure 3A:
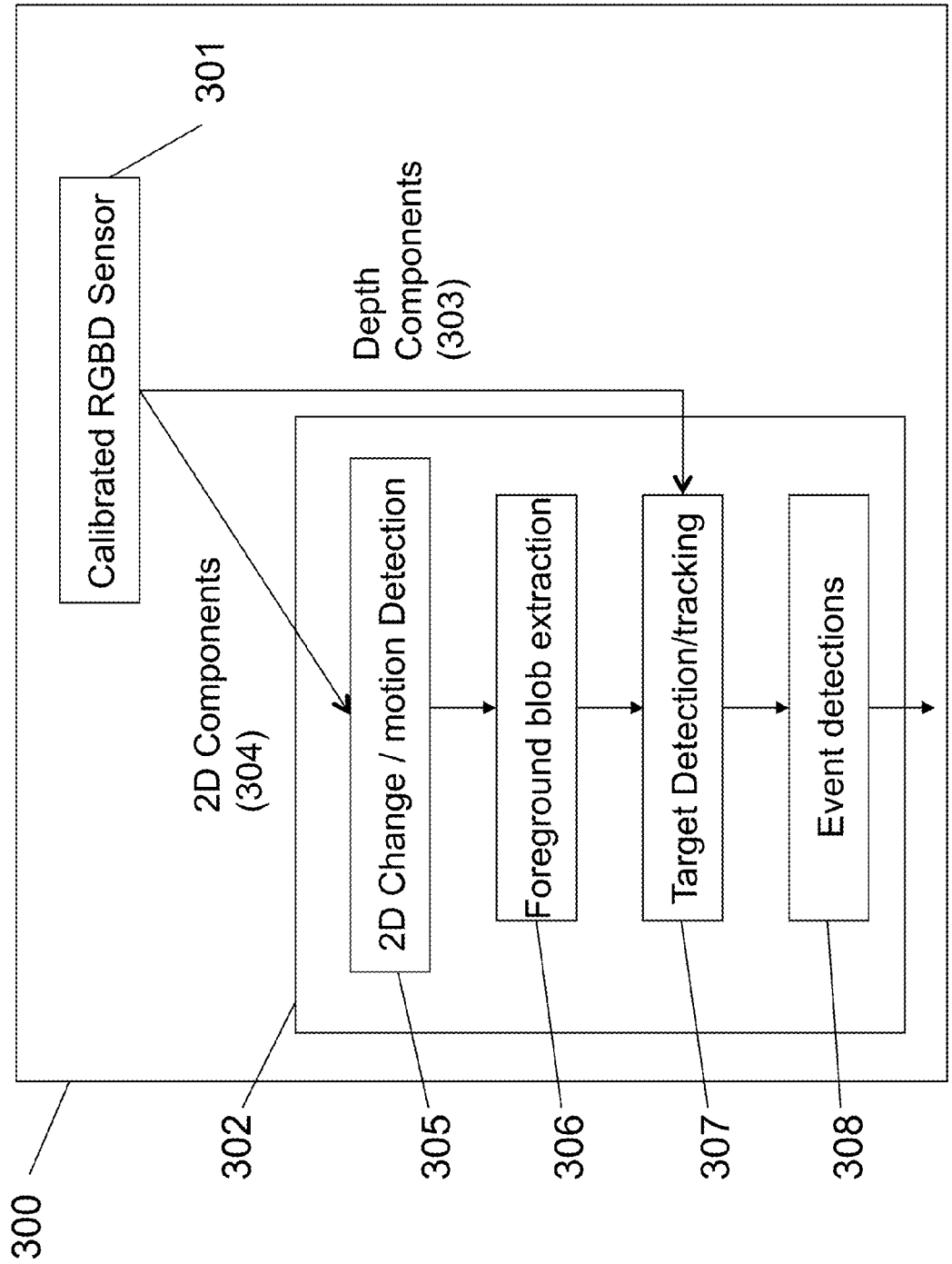
FIG. 3A shows a conceptual block diagram of a video surveillance system and method using one or more sensors that capture two-dimensional (2D) image data and depth data, according to certain exemplary embodiments.

FIG. 3A shows a conceptual block diagram of a video surveillance system 200 and method using, for example, an RGBD sensor or one or more other sensors that capture two-dimensional (2D) image data and depth data. In one embodiment, RGBD video frames are captured by and received from a calibrated RGBD sensor 301. Though one sensor is shown in FIG. 3A, video frames may be received from a plurality of sensors. For each image pixel of a video frame, the RGB components and the depth component may be determined. The RGB components and the depth component may come from a same device, like the one introduced in U.S. Pat. No. 8,320,621, or from separated devices and computed through additional procedures, for example, by a disparity map from stereo cameras. Although RGB type data is mainly discussed herein, the 2D image data captured by a camera and used in the video content analysis system and method disclosed herein can be other types of color data or other types of 2D data. RGB is used herein merely as an example.

In one embodiment, the RGB components 304 may be processed by existing video content analysis algorithms, such as like described in U.S. Pat. No. 7,825,954, to Zhang et al., published on Nov. 2, 2010, the contents of which are incorporated herein by reference in their entirety. As such, the system may analyze the 2D (e.g., RGB) components 304 to first perform motion and change detection (step 305) to separate foreground from background. For example, in one embodiment, pixels that are detected as moving are indicated to be foreground data (e.g., by being labeled with a logic value, such as "1"), and pixels detected as non-moving are indicated to be background data (e.g., by being labeled with a different logic value, such as "0"). The output of step 305 may include a foreground mask for each frame. Next, the foreground regions may be divided into separate blobs by blob extraction (step 306). During blob extraction, in one embodiment, the individual foreground pixels are grouped spatially. Foreground pixels that are touching or close to each other are assumed to correspond to the same object and are combined into a single blob. As a result, for each frame, one or more blobs may be detected. Each blob or a part of each blob may correspond to one or more targets at each timestamp (where, for example, a particular timestamp may be associated with a frame of the video). In target tracking step 307 targets may be detected based on the blobs extracted in step 306, and each target may be tracked, where each target may correspond to an object in the scene that is desired to be tracked. The depth component 303 is used here to provide a more accurate determination of which blobs correspond to targets, as opposed to, for example, which blobs correspond to objects that are not targets and do not need to be tracked. Additionally, the depth component 303 may be used to better distinguish different targets from each other. Finally, event detection step 308 performs event detection based on user-defined rules and the targets detected and tracked in step 307.

As a result of the above steps, the following method may be performed. First, a video sequence that includes a plurality of frames may be captured, for example, by an RGBD sensor, such as a camera having depth detection capabilities. Each frame may include a video image that includes depth-enhanced video data. For each frame, two-dimensional (2D) image data (e.g., RGB data) may be extracted, and also depth data may be extracted. The 2D image data and depth data may then be transmitted to and received by a video content analysis system (e.g., one or more processors executing one or more algorithms for analyzing video content). The 2D image data of the video sequence may then be processed to differentiate foreground data from background data and to detect one or more blobs comprised of the foreground data. The one or more blobs may correspond to one or more real-world objects, and correspond to one or more potential targets. For each detected blob, the depth data may be used to determine whether at least part of the blob corresponds to at least part of a target, or to determine whether to track at least a part of the blob as a target. For example, it may be determined that an entire first blob corresponds to a single real-world object, and so that the first blob is determined to correspond to a first target. Alternatively, it may be determined that a first blob actually corresponds to two different real-world objects, and so part of that first blob is determined to correspond to a first target, and another part of the first blob is determined to correspond to a second target. In a third case, a blob may be determined to correspond to only part of a real-world object, and so that blob and an additional blob may collectively be determined to correspond to a single target.

After it is determined that at least part of a blob corresponds to at least part of a target, the target is tracked and at least one event associated with the target is detected.

As discussed in the examples above, a video sequence may be received that includes a plurality of frames, each frame including a video image. For each frame, image data of the video image and also depth data associated with the video image may be received (e.g., it may be extracted from the video sequence and received by a video content analysis system). The image data may then be analyzed to detect one or more objects depicted in the video sequence (e.g., a blob may be extracted, and the system initially assumes that the blob corresponds to a real-world object in the video sequence, for example, by treating the blob as a potential target). Next, using the depth data along with the one or more detected objects, at least a first object of the one or more detected objects is classified as an object to be tracked. For example the first object may be classified as a person to be tracked, an adult to be tracked, a vehicle to be tracked, etc. The object to be tracked may be treated as a target. Next, tracking is performed on at least the first classified object. Finally, event detection analysis is performed on the first classified object. In certain embodiments, the video content analysis described above is automatically performed by a computer system, such as a video content analysis system.

In one embodiment, the depth data 303 is may be used in step 307 to help the target detection and tracking processes. The inputs to step 307 may be foreground image blobs extracted from the video frames based on change and motion detection. Each image blob may include a group of connected foreground pixels representing all or part of a physical object, or multiple physical objects. A correct understanding on what each image blob represents may be important for the overall system performance. The disclosed embodiments use the depth data to help make the correct decision in step 307 regarding which targets to track.

Figure 3B:
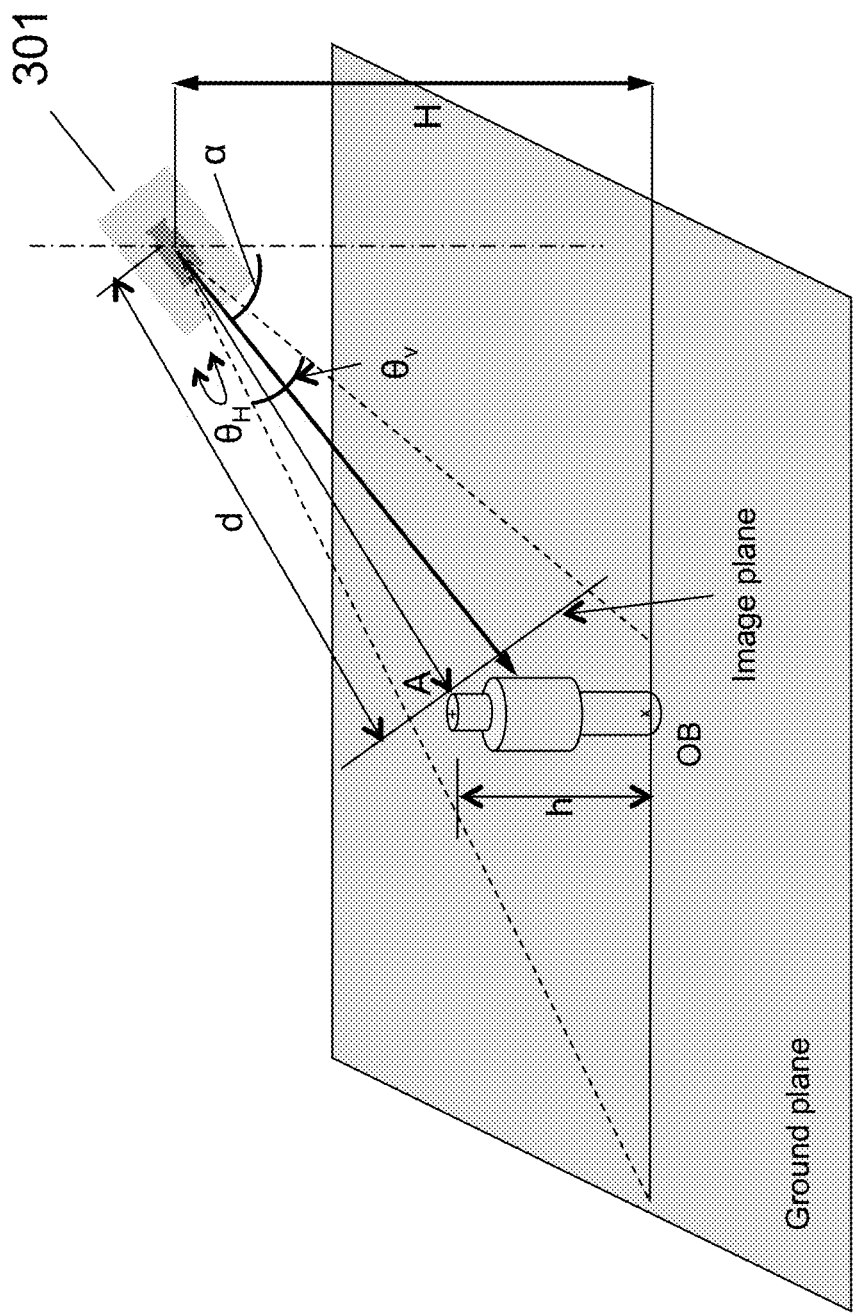
FIG. 3B depicts an example of depth information that can be used in a video content analysis system, according to certain embodiments.

FIG. 3B depicts one example of depth information that can be used to assist in deciding which targets to track. For example, FIG. 3B shows a camera device 301 mounted at a particular location (e.g., a ceiling). The camera device has a particular height (H), vertical and horizontal camera field of view angles ($\theta_H$, $\theta_V$), and camera tilt angle ($\alpha$). The camera device may include, for example, an image capture portion, such as a standard digital or analog camera, and a depth detection portion, such as an infrared detector as described above, stereo vision technology, or other known devices for directly measuring the depth and distance of objects in a three-dimensional space. In one embodiment, for example, camera device 301 is a calibrated RGBD sensor with a known camera height H, tilt up angle $\alpha$, and image horizontal and vertical field of views (e.g., known field of view angle and known number of pixels in the field of view). In one embodiment, an object (OB) has a particular shape and a height (h). The height (h) may not be initially known based on 2D data alone. To determine the height, a depth map may be created for the pixels that correspond to a detected blob that represents the person. In one embodiment, each pixel of a blob may be associated with a particular three-dimensional real-world coordinate that indicates the actual location of the object or part of the object that the pixel represents. As such, the distance between the camera and each real-world object represented by one or more pixels can be determined, and using the calibration information and the distance, a height of each pixel or each object represented by one or more pixels can be determined.

As shown in FIG. 3B, a three-dimensional coordinate, and thus a real-world height, at point A, which may correspond in one embodiment to the top of a person's head, can be determined by applying geometric equations that include as variables the calibration values (H, $\alpha$, $\theta_H$, and $\theta_V$) and the distance (d), also referred to herein as depth. As a result of the determined height, additional filtering or analysis can be performed. For example, a better determination can be made as to whether the object is actually a person (e.g., as opposed to a shadow or reflection).

Figure 4A:
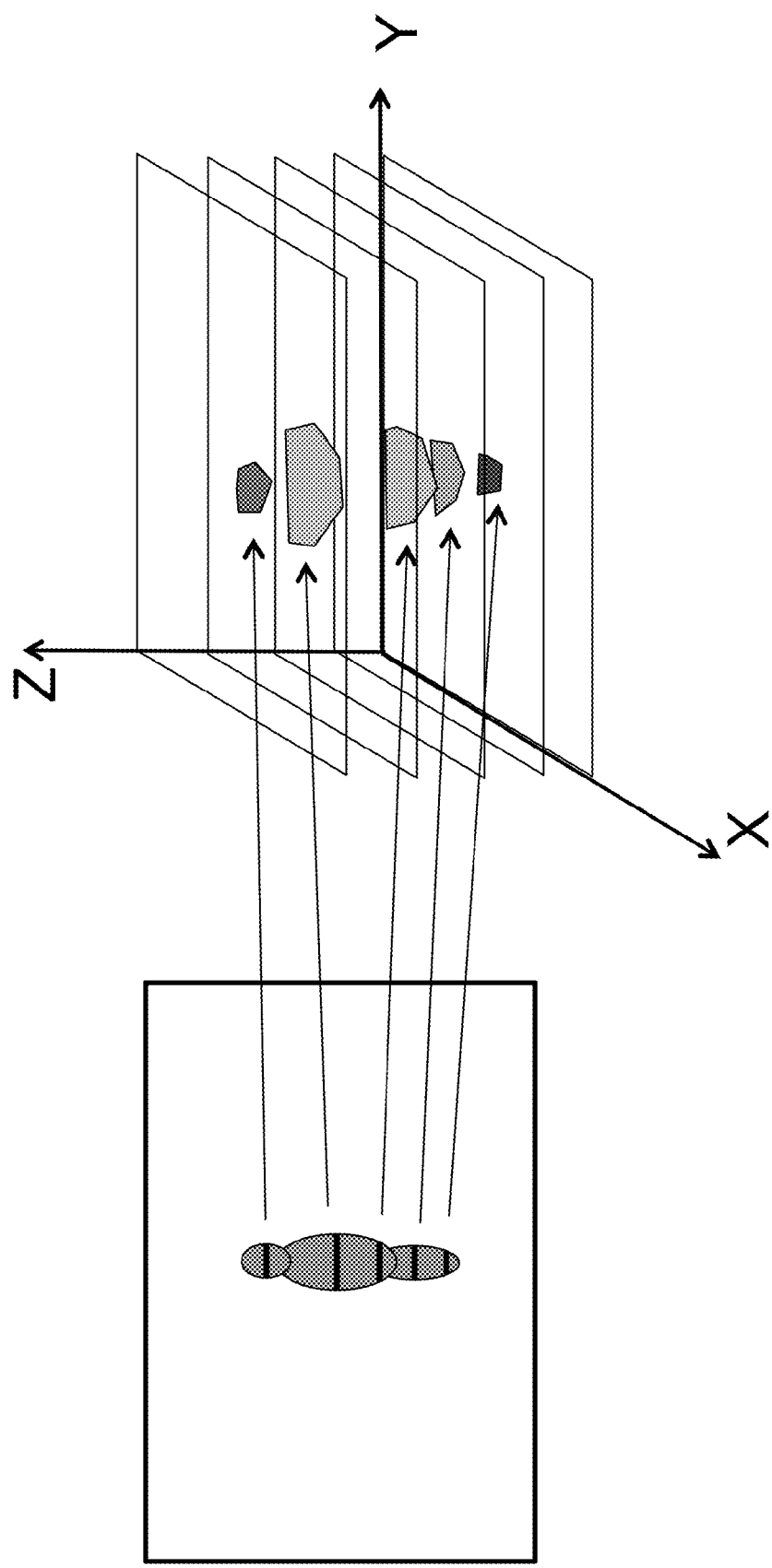
FIG. 4A depicts an exemplary mapping of some samples of image pixels in a blob onto a number of Z-planes in 3D space.

In one embodiment, the physical properties associated with an image blob are estimated by mapping some samples of the image pixels in the blob onto a number of Z-planes in 3D space as illustrated in FIG. 4A. Each Z-plane corresponds to a physical plane parallel to the ground plane. Each point on a Z-plane will have the same physical height in 3D space. The process quantizes the 3D space along the Z axis into a number of 2D planes which are named as Z-planes. The quantization step and the number of Z-planes used may depend on the physical size of the object under investigation. For example, the quantization step can be one foot for human size targets. The quantization step may also depend on some specific requirements of a particular desired detection scheme. For example, if one wants to detect a left behind bag that may be less than one foot in height, a smaller quantization step may be used.

Figure 4B:
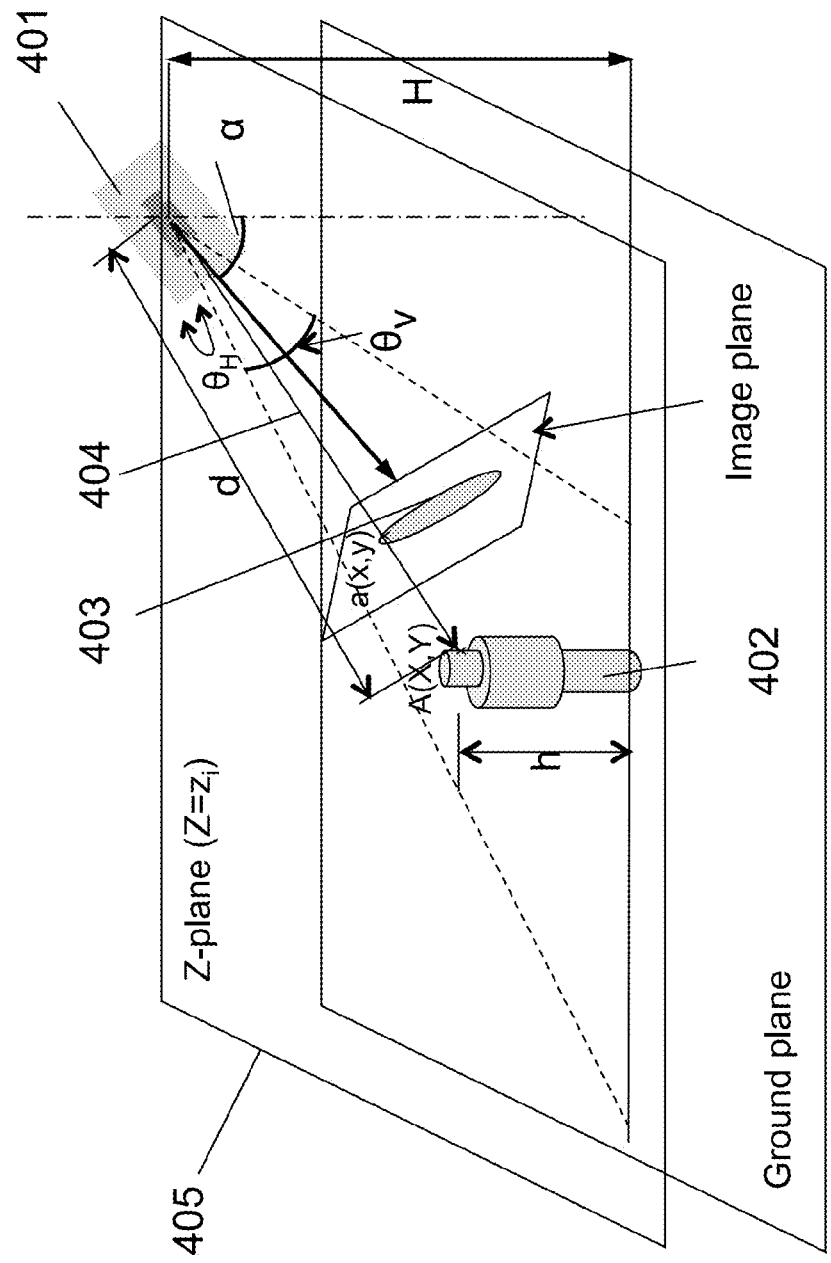
FIG. 4B depicts one example of how to map a pixel in an image blob onto a corresponding Z-plane in physical space, according to one embodiment.

FIG. 4B illustrates one example of how to map a pixel in an image blob onto the corresponding Z-plane in physical space. This mapping method may be implemented using a camera device 401 similar, for example, to that discussed above in connection with FIG. 3. In one embodiment, for example, camera device 401 is a calibrated RGBD sensor with a known camera height H, tilt up angle $\alpha$, and image horizontal and vertical field of views (e.g., $\theta_H$, and $\theta_V$). Both the RGB image of video frames and the depth measure for each pixel are provided by the sensor. For example, a human object 402 in the view may be detected as an image blob 403 after step 206 of the method 200 in FIG. 2. For one particular pixel a(x,y) in the image blob 403, the positional direction of the pixel from the camera's point of view 404 can be computed based on its image position (x,y) and the known camera horizontal and vertical field of views. This directional information is then combined with the camera height H, the tilt up angle $\alpha$, and the pixel depth data d to compute the corresponding 3D location (X, Y, h). Once this 3D location is determined, then the point A(X,Y) can be projected onto the closest Z-plane to the height h. The point A(X,Y) becomes one of the sample points of the blob 403 on that plane (e.g., indicated as the Zi-plane 405 in FIG. 4B).

One advantage of the disclosed embodiments is that not every pixel in the RGB image needs to be mapped onto the Z-planes. For example, in one embodiment, only the foreground pixels that represent the image blobs are to be projected onto the discrete Z-planes, and background pixels do not need to be projected onto Z-planes. In addition, because the number of Z-planes mapped is quantized, not every pixel associated with a blob needs to be projected onto a Z-plane. Further, as described further below, convex hulls may be used to represent the object regions on Z-planes. One convex hull may be approximated by a few pivot points, and not every pixel of a blob in a particular Z-plane needs to be sampled in order to form the convex hull. Thus pixel sampling may be performed for each frame and within each image blob to further reduce the computational complexity. In addition, this approach relies less on the accuracy and completeness of the depth data on every image pixel, and is thus more robust despite inaccuracies that may be associated with the depth information.

The samples on a Z-plane mapped from the corresponding pixels from the same image blob may form different spatial regions on the Z-plane because they may correspond to spatially separated objects. FIG. 5A shows one example of two separate sample groups on a Z-plane. A clustering process may be used to group these Z-plane samples into separate regions as illustrated, for example, in FIG. 5B. In one embodiment, a fast clustering method using the convex hull blob representation is performed. A convex hull may be used to represent each sample cluster. Its convex boundary defines the object blob on the Z-planes. In one embodiment, the physical distance between a sample and an existing sample or cluster is used to perform the clustering.

FIGS. 6A-6C illustrate an example of a definition of the distance between a sample point and an existing, already-determined convex hull region, and the method to compute the distance. In FIG. 6A, 601 is the convex hull of one existing cluster, 602 is the current sample under consideration, if 602 is inside 601, the distance is considered as 0. If the current sample point is outside of an existing cluster, as illustrated in FIGS. 6B and 6C, the closest pivot point may be searched for first, then the current sample point may be projected on to the two boundary lines which contain the closest pivot point. There are two cases in this scenario, as shown in FIGS. 6B and 6C. In FIG. 6B, 603 is the current sample under consideration, 604 is the closest pivot point, 605 and 606 are the two boundary lines containing 604, and 607 and 608 are the two projection points (e.g., each is the closest point between sample point 603 and its respective boundary line 605 or 606). In this case, both projection points are on the extension portions of the lines 605 and 606, not on the actual boundary of the convex region. The distance to the closest pivot point is then used as the distance to the cluster. In FIG. 6C, 609 is the current sample under consideration, 610 is the closest pivot point, and 611 and 612 are the two boundary lines containing 610. In this case, 613 is the projection point of 609 on 612 and it is on the boundary of the convex hull. Thus the distance between 609 and 613 is considered as the distance between the sample point and the existing cluster. As a result of these calculations, the distance between the sample point 603 and the cluster can be thought of as a minimum distance among (1) the distance between the sample point 603 and a closest pivot point, and (2) a shortest distance between the sample point 603 and a convex hull boundary.

A physical distance threshold may be used to determine whether a sample point outside the cluster should belong to the cluster. Thus the clustering process can be described as follows. Given a list of sample points on a Z-plane (at the same height) that are mapped from sample pixels from an image blob, select a first sample and consider it as the first sample cluster. Then iterate through all the remaining sample points. For a given sample point, compute its distance to all the existing blob clusters. If the distance to a cluster is less than a distance threshold predetermined as a parameter, update this cluster by including this sample into the cluster convex hull. If one sample belongs to multiple clusters, merge all the corresponding cluster convex hulls into a new cluster. If a sample does not belong to any existing clusters, create a new cluster using the current sample. The exemplary method is a one-pass clustering process, and the distance computation only involves a limited number of pivot points. As a result, the clustering process, and the resulting target detection and tracking is computationally efficient.

Figure 7:
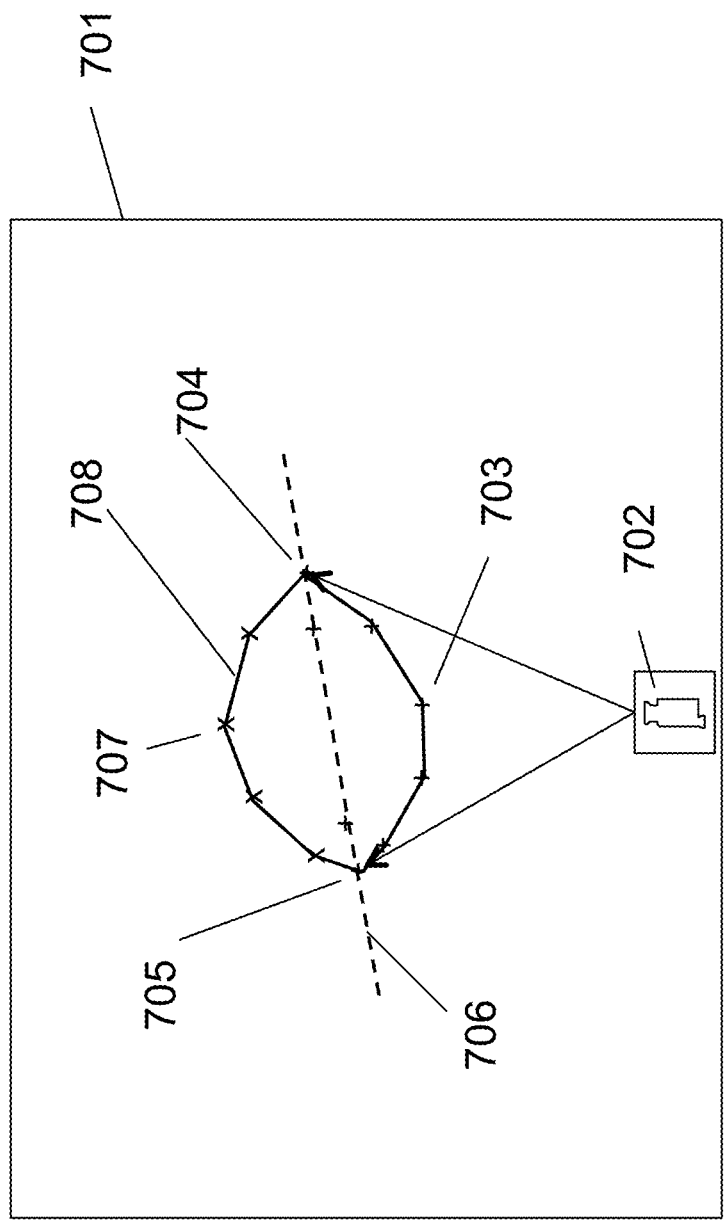
FIG. 7 shows a method of determining a blob convex hull on a Z-plane for one camera location, according to certain exemplary embodiments.

Since a typical RGBD camera is not able to see through an object, a self-occlusion issue often occurs in the 3D space representation of an object. FIG. 7 depicts an exemplary method of addressing this self-occlusion problem. FIG. 7 shows a Z-plane 701 determined based on a camera location 702. The pivot points of an observed convex cluster obtained through the above mapping process are marked as "+". For example, one of these pivot points is indicated as 703. Looking from the camera 702 point of view (wherein the camera is placed a particular distance in the X-Y direction from the object represented by the cluster), 704 is the right most pivot point and 705 is the left most pivot point. These two points are used to determine the self-occlusion line 706. Next, for all the pivot points between the self-occlusion line and the camera, their mirror points on the opposite side of the line 706 are computed and marked as "x", for example, 707 is the mirror point of 703, the final convex cluster 708, is determined by both the original pivot sample points and the mirror sample points. The object self-occlusion is more severe when the camera view is oblique.

Figure 8:
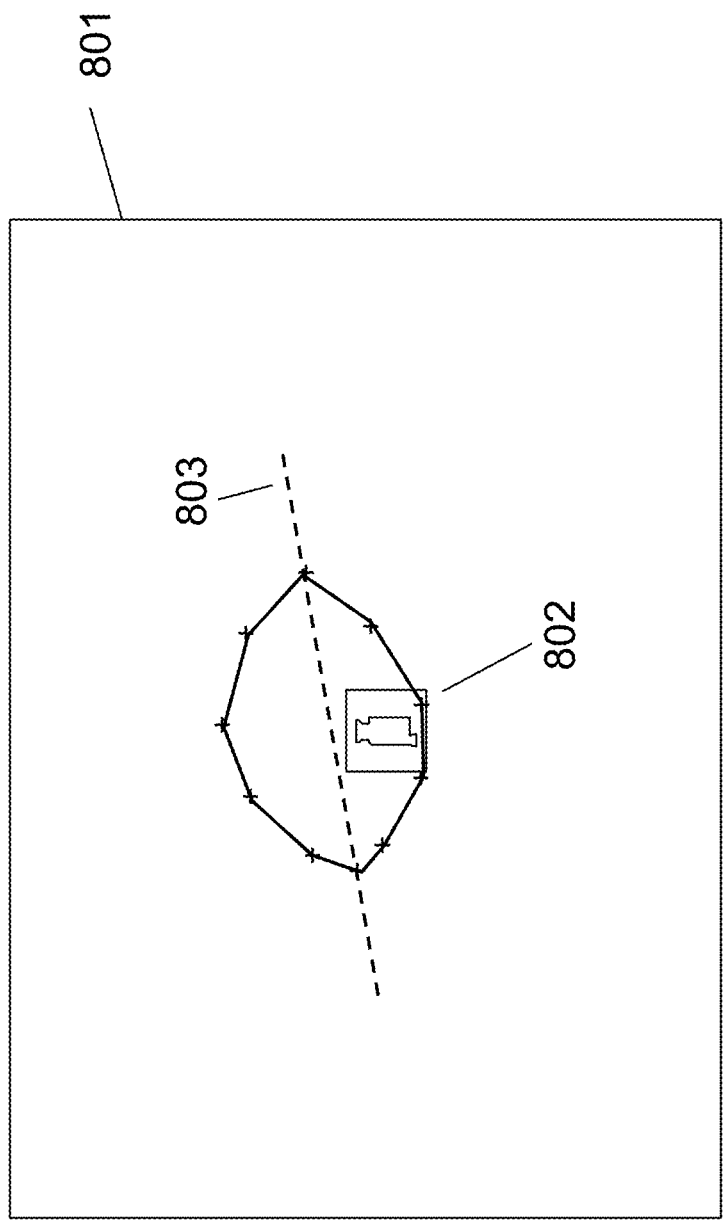
FIG. 8 shows another example of determining a blob convex hull on a Z-plane for another camera location, according to certain exemplary embodiments.

In certain embodiments, a camera position may be directly above part of an object, or almost directly above the object. FIG. 8 shows an almost overhead camera view case, where 801 is the Z-plane, and 802 is the projected camera on the Z-plane. Although there is still a self-occlusion line 803, no extra mirror pivot points are generated because the camera 802 is inside a Z-plane blob cluster and is very close to the self-occlusion line. Thus, the amount of self-occlusion compensation on each Z-plane is adaptive to the camera position and viewing direction, and this compensation process can provide a more accurate measurement on the projected physical size of the object on each Z-plane.

Figure 9:
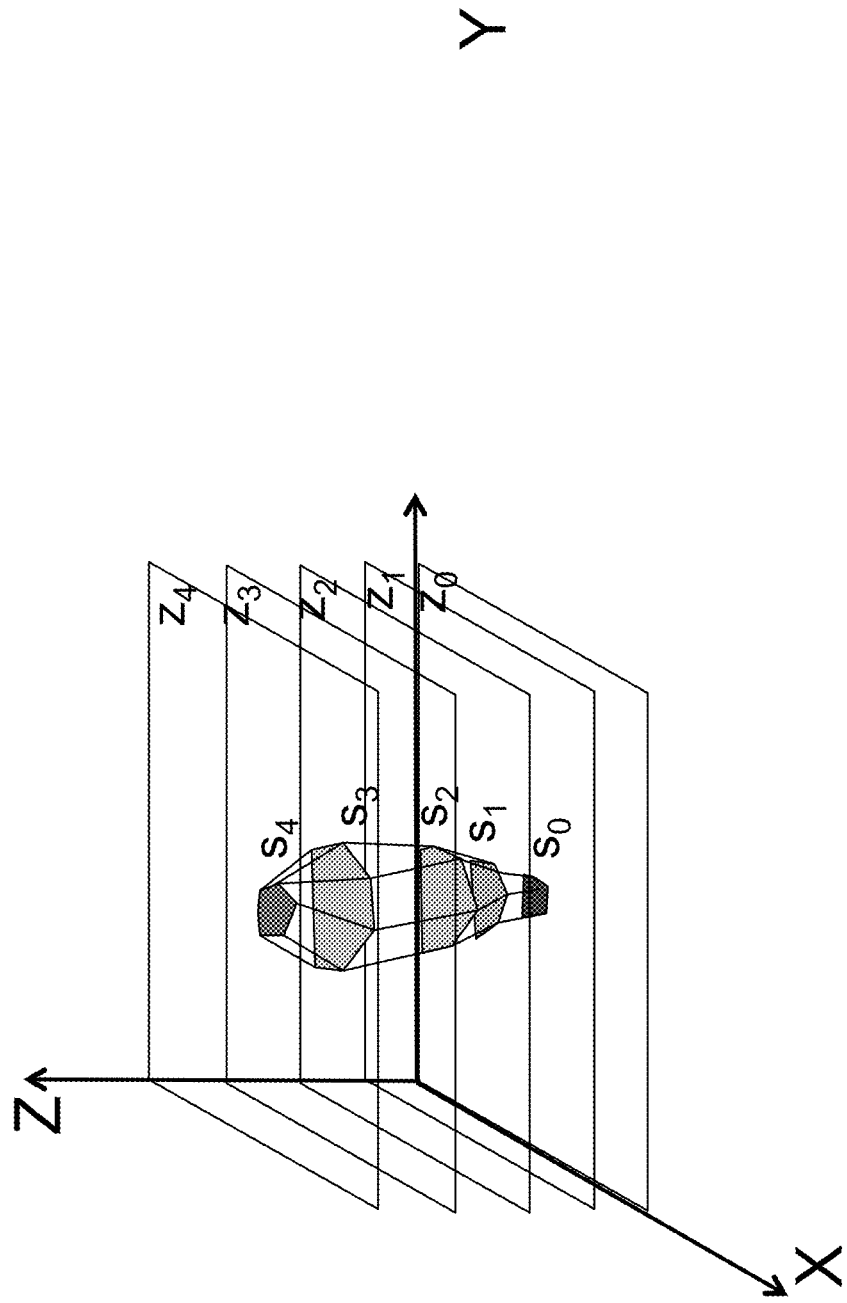
FIG. 9 depicts an example of an image blob and its projected convex hull slices on a list of corresponding Z-planes, according to one exemplary embodiment.

FIG. 9 illustrates an example of an image blob and its projected convex hull slices on a list of corresponding Z-planes. The physical volume of the image blob can be further computed using these convex hull slices on the Z-planes. For a given image blob, assuming there are N Z-planes denoted as $Z_0, Z_1, \ldots, Z_{N-1}$, and on each plane the corresponding convex hull slice area is $S_i$, then the physical volume of the blob can be estimated as:

$$V = \sum_{i=0}^{N-2} (S_i + S_{i+1}) * (Z_{i+1} - Z_i)/2$$

The physical volume measurement may be used, for example, to perform target filtering and target classification. For example, it can increase the confidence on detecting a human object. A human blob should have a physical volume close to an average physical human. The change of human postures will change the image appearance but typically will only have small impact on the human volume. Meanwhile, the human pose change can be detected by tracking the changes of physical height and the projected areas on different Z-planes. The physical height and volume measurements can also be used to distinguishing different types of people from others, such as children from adults.

The physical volume measure may also be used to filter out spurious foreground blobs caused by illumination factors, such as shadows and reflections. These types of non-legitimate blobs usually have little physical volume. The physical height and volume information can be used to detect other types of targets such as vehicles or shopping carts, for example. The physical sizes at different Z-planes are strong clues and may be used to detect objects with different physical size and shapes. Just using a height map without volume information may incorrectly detect a shadow on a wall as a person.

Figure 10:
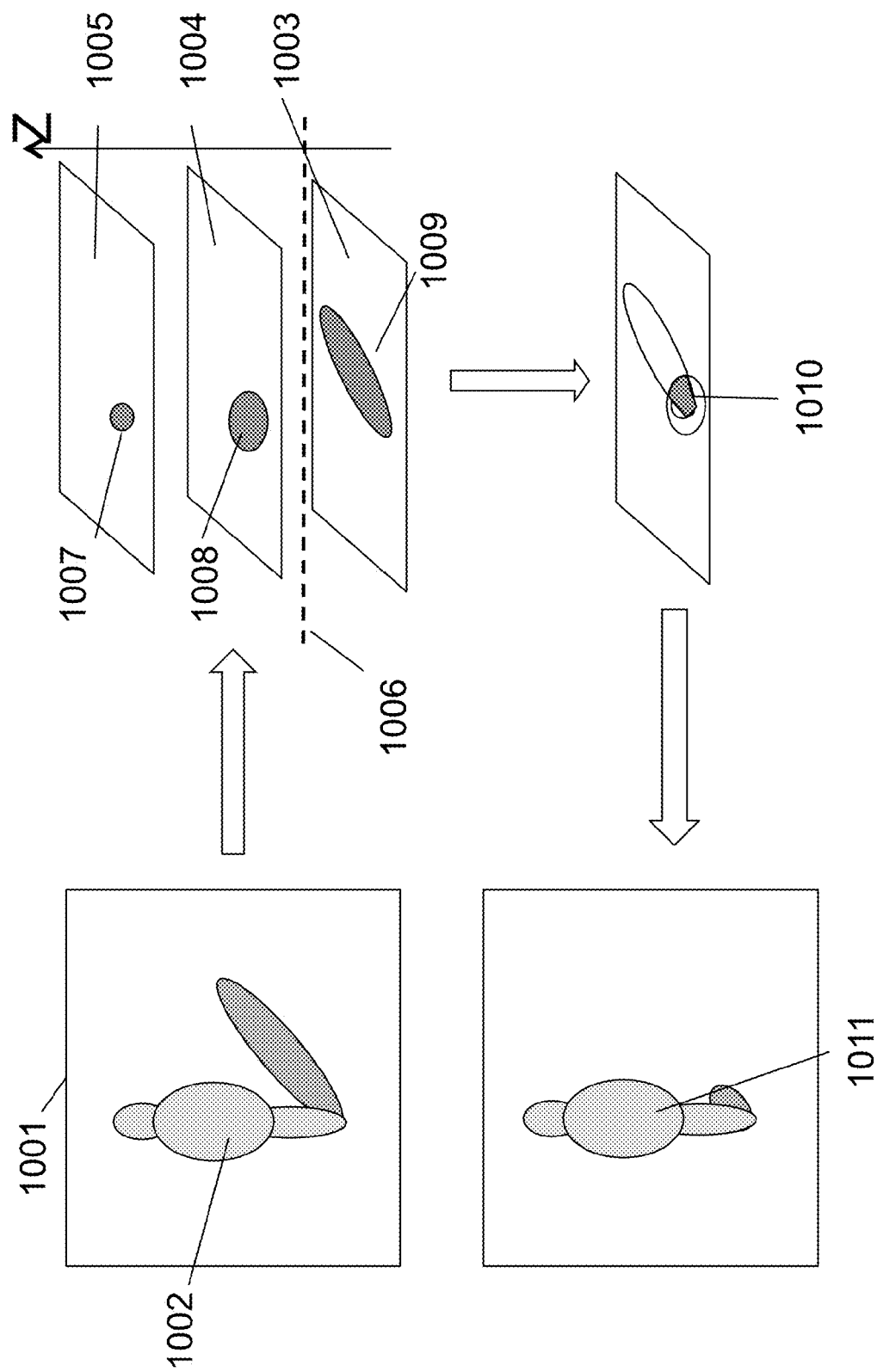
FIG. 10 shows one example of how to remove shadows in an image blob, according to one exemplary embodiment.

FIG. 10 shows one example of how to remove shadows in an image blob. An RGB image 1001 may include a detected foreground image blob 1002, which corresponds to both a human object and its shadow casting on the ground. Without the depth analysis, the system would have difficulty on understanding what type of object the blob represents. Therefore, in one embodiment, to remove the impact of shadow, first, the image blob is projected onto a number of Z-planes indicated as 1003, 1004, and 1005. A height threshold 1006 is used separate the Z-planes into ground plane and non-ground planes. The height threshold 1006 may be slightly higher than the actual height of the ground to take into consideration minor variations of ground height (e.g., non-uniform flooring height, or the addition of carpeting or matts to the floor). For example, the height threshold may be less than one inch or less than two inches above a floor height. The height threshold 1006 may vary over the frame of the image to take into consideration different levels of the floor/ground (e.g., a first height for a parking lot level delivery parking spot and a second height for a warehouse floor height to accept goods from a truck parked in the parking spot). The height threshold 1006 may gradually change over the floor/ground to take into consideration slopes (e.g., a graded parking lot). Blob slices 1007 and 1008 on the non-ground planes, and blob slice 1009 on the ground plane are determined as blob slices for the blob 1002. The blob slice on the ground plane is likely to be a shadow or reflection. Therefore, to remove the potential shadow and reflection from consideration, the blob slices 1007 and 1008 are projected on to the ground plane, for example, from a top-down view. The projected regions create an overlapping region 1010 with the original ground-plane blob slice 1009. The overlapping region 1010 is then used as the estimated blob slice representing the actual object on the ground plane, instead of the original blob slice 1009. Blob regions 1007, 1008 and 1010 can then be projected back onto the image 1001 to refine the original blob 1002 to appear as blob 1011, where most of the shadow part is ignored. The physical volume of the refined blob 1011 can be also computed using 1007, 1008 and 1010.

Figure 11:
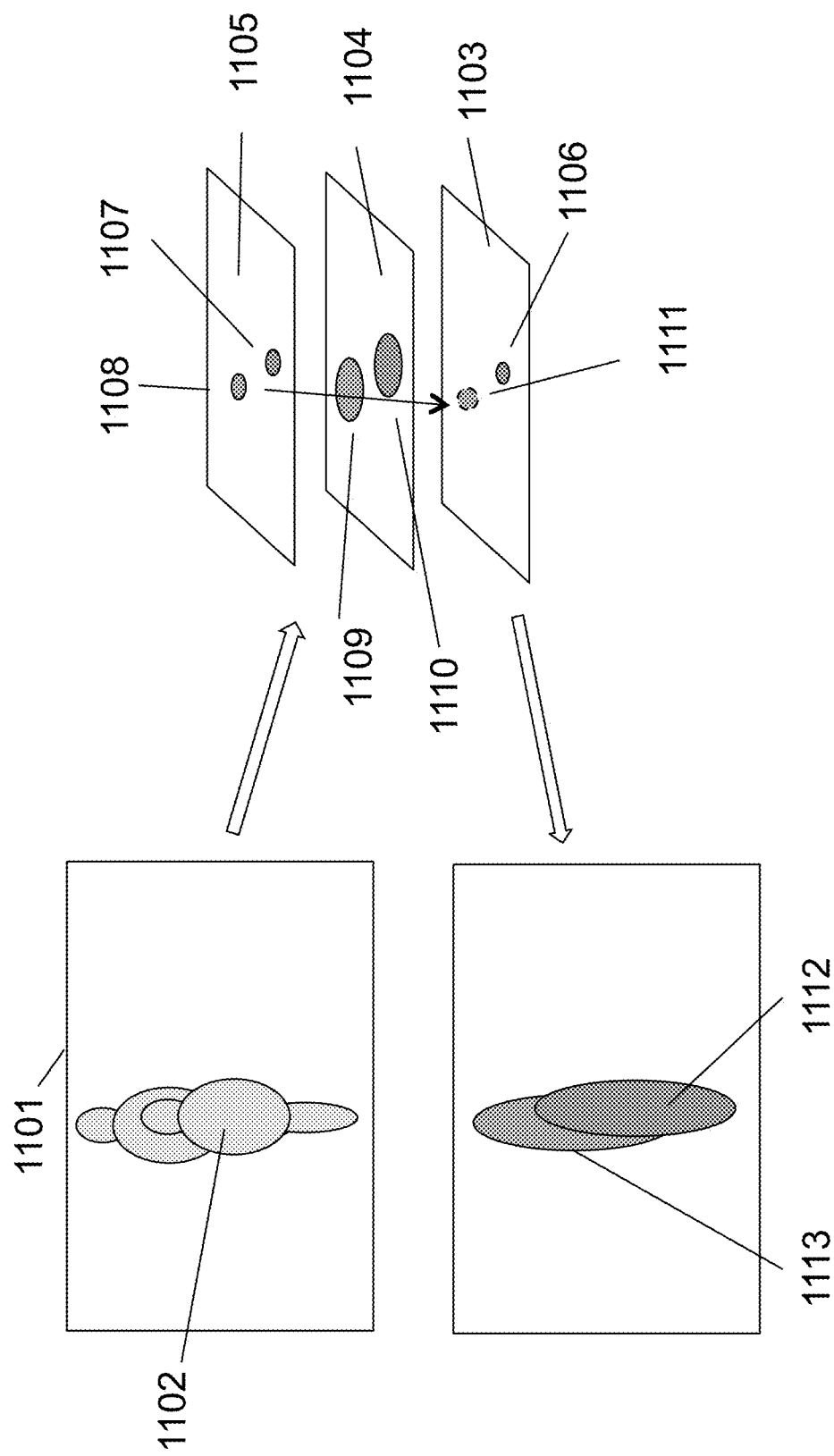
FIG. 11 shows a method of performing blob split on a two-dimensional image using depth information associated with the blob, according to one exemplary embodiment.

Due to the camera viewing perspective, multiple targets not close to one another may be connected in an RGB image and appear as a single blob. In one or more embodiments, they can be separated in the RGB image by using the depth data. FIG. 11 illustrates a method splitting a single blob of an RGB image corresponding to multiple targets using the depth information associated with the blob. An RGB image 1101 includes a detected foreground image blob 1102, which contains two human targets that are separated in physical space. In the RGB image space, however, these two human objects are connected and it is difficult for the system to understand whether there is a single large human target or there are multiple human targets with occlusions. Though techniques like facial recognition may be used in some cases to resolve this question, in some cases, facial recognition may fail (e.g., if the two people have their backs to the camera). By mapping the image blob on to a list of Z-planes 1103, 1104 and 1105, the system may determine that on some Z-planes 1104 and 1105, the two human objects are separated as they are clustered into different blob regions, indicated by 1107, 1108, 1109 and 1110. This is because in reality, the two objects are separated in space. The depth data is used to separate them out on the Z-planes during the video content analysis. This separation in Z-planes provides strong evidence that the image blob 1102 consists of two human objects instead of one. The separated blob regions on the list of Z-planes are then grouped into two physical objects by checking their spatial overlaps. Those regions whose projected region on the ground plane overlaps with each other may be considered to be from the same physical object. For the object (1108, 1109) that does not have a ground plane blob region, the projection from its top plane region 1111 may be used to indicate its ground location. Thus in this example, 1106, 1107, and 1110 correspond to one human object 1112, and 1108, 1109, and 1111 determine another human object 1113 in image 1101. The blob regions of 1112 and 1113 may be obtained by back-projecting their corresponding blob regions on the Z-planes onto the original image. As a result, the physical measurements of the targets represented by the two blobs may be obtained.

Figure 12:
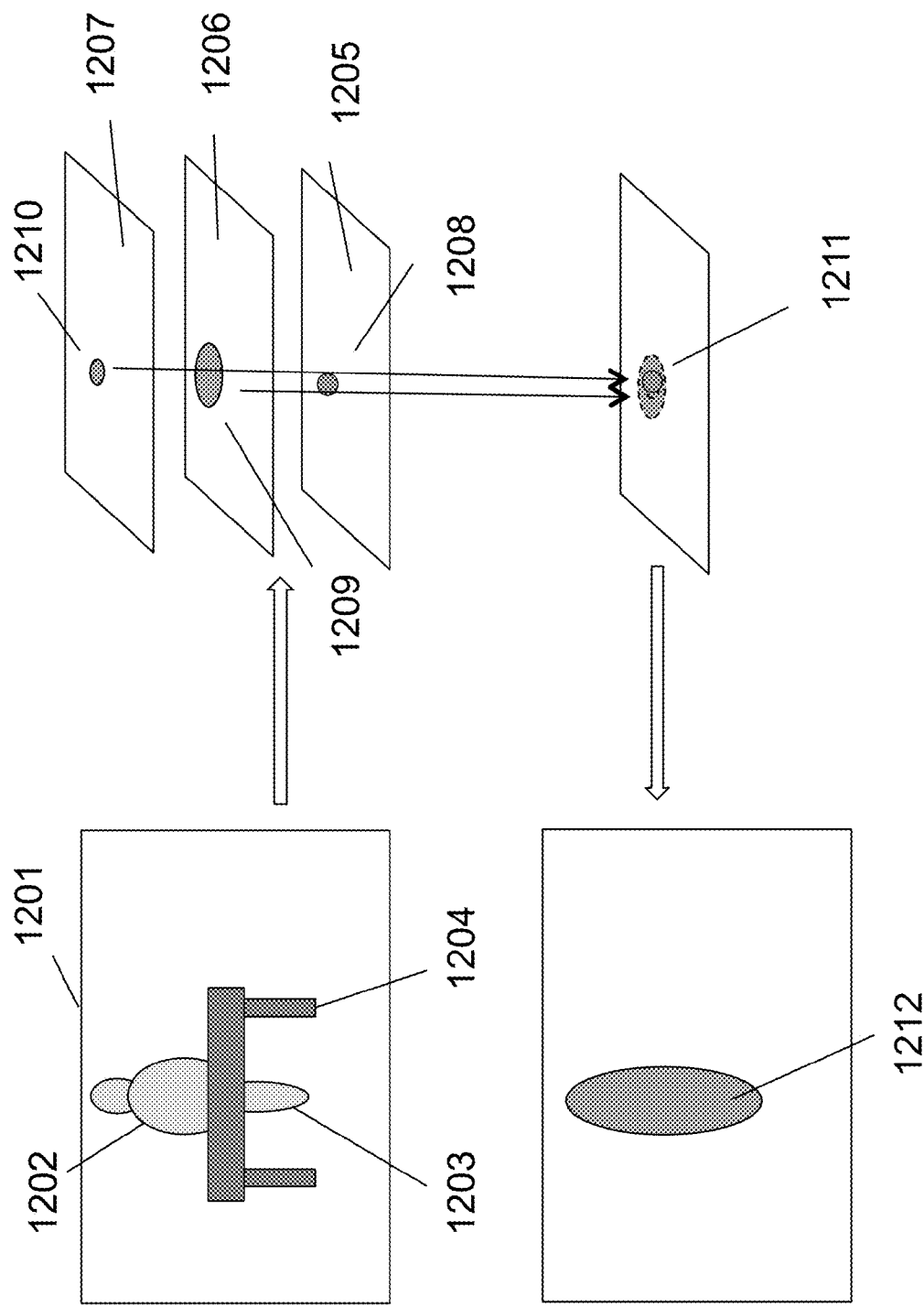
FIG. 12 shows an example of how to merge two falsely separated image blobs, according to one exemplary embodiment.

In some other scenarios, a single foreground object may be occluded by a static background object, or part of the object looks so similar as the background that the system may miss-detect that part as foreground. When these happen, the RGB-based system will likely break a single image object into multiple image blobs. This type of problem may also be solved by the depth analysis. FIG. 12 shows an example of how to merge two falsely separated image blobs, according to one embodiment. An RGB image 1201 includes a static background object 1204 which occludes a human object in the scene and causes the system to detect two separated blobs 1202 and 1203. These two image blobs are projected onto the Z-planes 1205, 1206 and 1207. Blob 1203 has a corresponding blob slice 1208 on Z-plane 1205, while blob 1204 has corresponding blob slices 1209 and 1210 on the other two Z-planes. When projecting these blobs onto the ground Z-plane, they all overlap with one another. Further, the physical volume measured by these projected regions on the Z-planes is very close to that of a human object. This provides strong evidence that 1202 and 1203 actually correspond to a same human object. Thus a blob merge operation may be performed in the image 1202 to create a single blob 1212 which can be classified as a target such as an individual human object.

Figure 13:
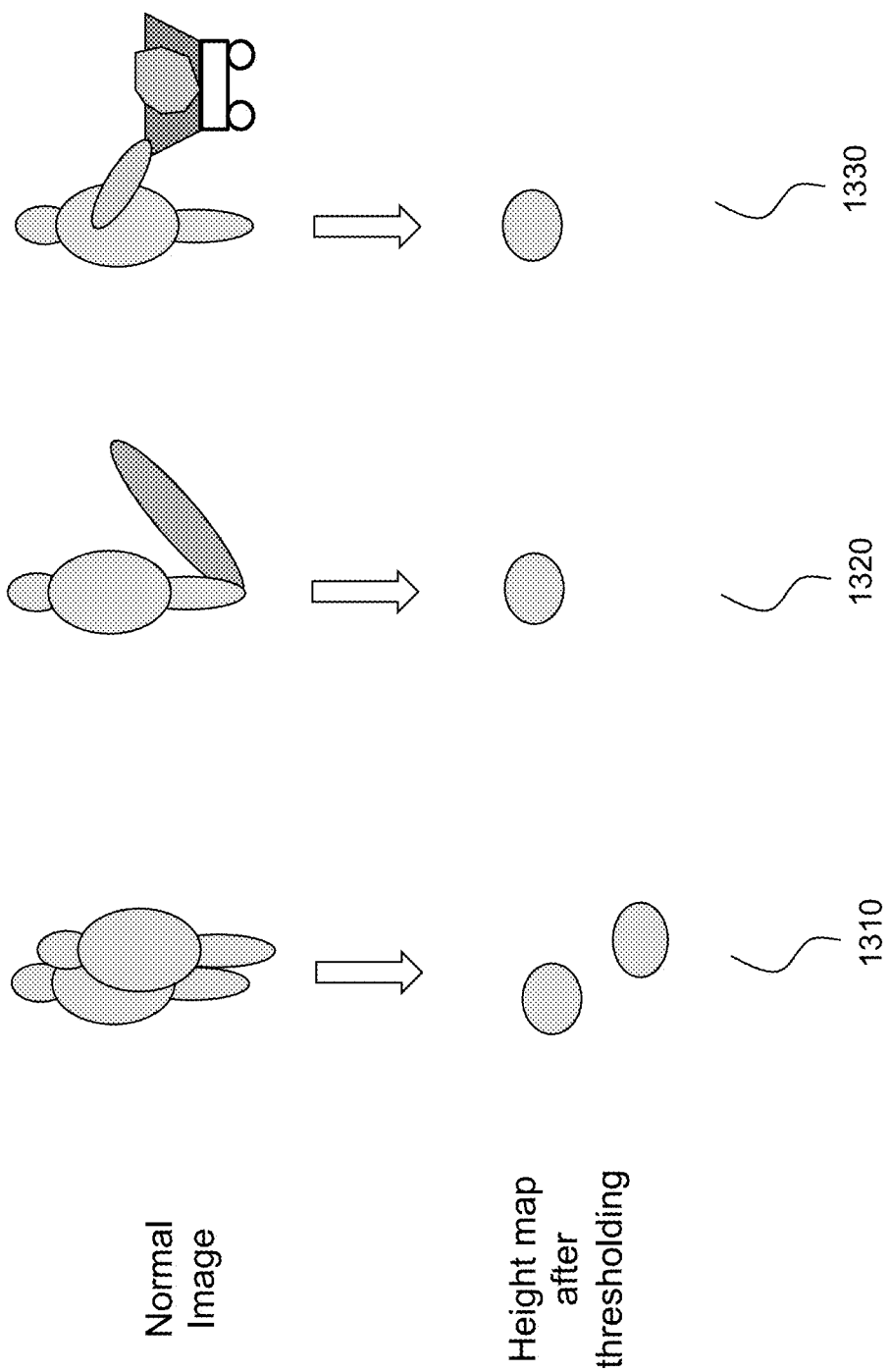
FIG. 13 shows one example of an application of a combined calibration and depth detection system such as described in FIGS. 1-12, according to one embodiment.

One example of a general application of the combined calibration and depth detection system is shown in FIG. 13. As shown in FIG. 13, a height threshold can be applied to detected objects, and can be used to create a target map after the height threshold has been applied. For example, in situation 310, two people stand close together, one occluding part of the other. By applying calibration information and measured depth information to a captured image, a camera device or camera system can determine first that the image is of two targets, and second the height of both targets, and as a result, determines that two people are represented in the captured image. A resulting mapping of the people in the space (a depth map, or height map) can be generated. For example, the mapping may represent a top-down, two-dimensional view of a space, specifically showing the people above a certain height within the space and their location within the two-dimensional view.

In situation 320, however, one person stands in a space, but the person's shadow also appears on the floor. Because the depth detection can be used to remove the effects of the shadow (e.g., as discussed above), the shadow can be omitted from the mapping of people in the space in the depth map. Similarly, in situation 330, one person is partially occluded by a shopping cart, which also has a round object that may be detected as a potential person's head. However, after a height threshold is applied, the person is confirmed to be an actual person and may be tracked. However, after a height threshold is applied, the round object is assumed to not be a person and is not tracked or is tracked as shopping cart objects. Tracking shopping carts and detection of items being added thereto may be used to perform market research and/or determine the efficacy of merchandising (e.g., the effectiveness of advertising, displays, product presentations, product locations, etc.). Tracking shopping cars may be useful to detect theft, such as when a shopping cart has left the store (or other area inappropriate to leave without payment) when the shopping cart contains when it has not been detected that the shopping cart previously visited a checkout line or otherwise had been associated with payment activities. As a result, only one person is included in the mapping of people after the height threshold has been applied. Alternatively, only one person is mapped as an adult and other objects are mapped as with other classifications. In each of these examples (320 and 330) a vision only person counting system (without depth detection) may have counted two people, thus over-counting the number of people in two of the examples.

After objects are identified as targets, those targets may be tracked within a scene in a video. However, because of the height mapping, the tracking may be analyzed from a top-down, two-dimensional perspective, even though there is no camera capturing images from a top-down view looking directly down at the scene. In one embodiment, a standard Kalman filter can be used to track the location of each object.

Figure 14:
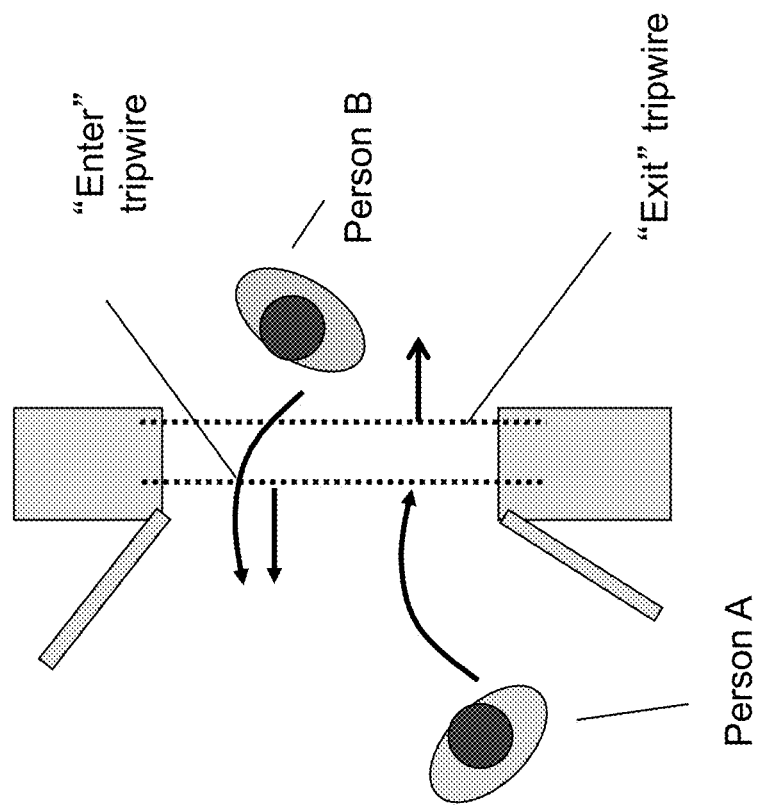
FIG. 14 shows another example of an application of a combined calibration and depth detection system such as described in FIGS. 1-12, according to one embodiment.

Event detection can then be performed based on the detected objects and their tracking information. For example, a virtual tripwire, as described in U.S. Pat. No. 6,696,945, issued to Venetianer et al. on Feb. 24, 2004, the contents of which are incorporated herein by reference in their entirety, can be used to perform counting of people moving in or out of a certain area. An example of a virtual tripwire is shown in FIG. 14.

Another example of a general application of the above embodiments is to perform object tracking to determine when a person falls down. For example, a captured image may have the shape and size of a person, but the height information (that may be obtained from depth information) may show that the person's head is near to the ground (e.g., one foot off the ground), may indicate that a person has fallen down or is lying down. As a result, the person can be mapped into the two-dimensional overhead view as long and narrow, as shown in FIG. 15. In the two-dimensional overhead view, objects can be represented using a color or grayscale scheme that indicates heights of certain objects, in order to show the topography of the objects in the image. As such, a top of someone's head may have a different shade or color from a point lower on the person's head.

In a further example, the embodiments described above, as well as height mapping could be used to more accurately determine queue length (e.g., the number of people waiting in a line). An exemplary queue is shown in FIG. 16. Because many of the people occlude others in the line, or blend in with the other people in the line, standard methods that employ only camera calibration to detect objects may not be able to accurately count or locate the number of people waiting in the line. But with the addition of a direct measurement of distance, for example, for certain pixels of interest in a captured image, a system that uses depth information to verify the classification of potential objects, as well as a height-mapping system can better determine the number of people and their actual location. The actual image (1610) can be then analyzed as a height map (1620).

A method of performing video content analysis (VCA) using the disclosed depth sensing VCA system is shown in FIG. 17. As depicted in FIG. 17, in step 1701, calibrated depth sensing is performed. For example, it may be performed by a camera device that employs an image capture portion and a depth sensor portion to determine a depth of certain objects in the captured image. Based on the depth, and/or other information determined based on the depth of pixels associated with certain objects (e.g., foreground objects), targets in a video sequence may be detected (step 1702). The detected targets can then be converted in step 1703 to a height, to determine the height of the object. The height information can then be used to assist in detecting whether the object is a particular target object, such as for example, a person. For example, an analysis component of the system can determine whether the detected object is above a threshold height, and if so, it can confirm the object as a person to be tracked. In step 1704, the target may be tracked. As a result, in step 1705, events can be determined based on the tracked target. Although certain steps in FIG. 17 are described in a particular order, the steps need not follow in that order. For example, in one embodiment, a height map of foreground objects may be determined prior to detecting targets to be tracked, and based on the height map and a height threshold, only certain targets are then selected to be tracked (e.g., a height map may indicate the heights of foreground objects such as people in the scene, and based on a height threshold such as 4 feet, in one embodiment, only adults are selected as targets to be tracked).

FIG. 18 depicts an exemplary method 1800 for performing building automation using a video content analysis system that uses depth sensing, according to certain exemplary embodiments.

As shown in FIG. 18, in order to provide automate building actions or alerts, certain events can be defined (step 1801). The events may be defined by a tenant, owner or a building manager who programs them into a computer, for example. The events may be defined according to the desires of the tenant or owner. The events may be singular events, such as "person detected," or may be based on collective information, such as "person detected after 9:00 PM" (indicating person detected after normal work hours). Many events can be set and examples are discussed elsewhere herein and need not be repeated here. Groups of events can be set, and rules can be set based on the events. Events can be set to include information from different rooms monitored by different cameras the building. As discussed below, many of the events are more accurately determined by using depth data along with two-dimensional image data to perform depth-enhanced video content analysis.

In step 1802, a plurality of video sequences are monitored from a plurality of video cameras. For example, each of cameras 111, 121, 131, and 141 in FIG. 1 may capture video sequences, two-dimensional image data as well as depth data may be obtained from the video sequences. The data may be obtained by a central computer system (within the building and/or remote), or may be obtained by processing hardware and software in the cameras themselves.

In step 1803, video content analysis steps are carried out on the two-dimensional image data to detect objects in the video sequences. For example, using analysis techniques such as facial recognition and shape analysis, the objects can be identified as particular targets. For example, a person in the video sequences can be identified as a person, or as a particular employee, occupant or tenant of the building.

In step 1804, depth data is used to confirm information about the detected targets. For example, in one embodiment, depth data may be used to determine a height of the target, which in turn can be used to determine a position of the target (e.g., sitting, lying down, standing up). Although step 1803 is depicted as occurring before step 1804, in one embodiment, steps 1803 and 1804 may occur in other order, (i.e., depth data is used to determine what portions of the video to analyze), or simultaneously, such that two-dimensional analysis is performed in conjunction with depth data confirmation to perform depth-enhanced video content analysis.

In step 1805, based on the information obtained in step 1804, an event may be detected (e.g., person detected in area A). Based on the events detected, certain rules can be set that trigger actions, alerts and/or alarms. Different types of and severity levels of alarms can be set based on different types of events.

To implement the system and methods described herein, various computing and optical components may be used, such as one or more of the following: a general purpose computer; supercomputer; a mainframe; a super mini-computer; a mini-computer; a workstation; a micro-computer; a server; an interactive television; a hybrid combination of a computer and an interactive television; a smart phone; a tablet; and application-specific hardware to emulate a computer and/or software. These may include one or more processors, one of more field programmable gate arrays (FPGAs), computer memory, a computer-readable medium such as, for example, any storage device used for storing data accessible by a computer (e.g., a processor may perform various algorithms on data received from a camera device, and a computer memory can then store the information about the various pixels and can store results of blob detection, target detection, and event detection). Examples of a computer-readable medium include: a magnetic hard disk; a floppy disk; an optical disk, such as a CD-ROM and a DVD; a magnetic tape; a memory chip; a solid state storage device; and a carrier wave used to carry computer-readable electronic data, such as those used in transmitting and receiving e-mail or in accessing a network. A tangible computer-readable medium includes computer-readable media, such as listed above, that are physically tangible. In addition, software may be used in combination with the computing and optical components to implement the methods described herein. Software may include rules and/or algorithms to operate a computer, and may include, for example, code segments, instructions, computer programs, and programmed logic. The various computers, cameras, and other image equipment described herein can be connected over a network, which may involve permanent connections such as cables or temporary connections such as those made through telephone or other communication links, and also may include wireless communication links. Examples of a network include: an internet, such as the Internet; an intranet; a local area network (LAN); a wide area network (WAN); and a combination of networks, such as an internet and an intranet. The various hardware and software examples described above are also described in greater detail in the patent documents incorporated by reference herein.

By including a depth as a component of the video content analysis, inaccuracies may be reduced. In addition, higher accuracy by use of a depth component has particular advantages with respect to certain video content analyses, such as monitoring buildings (interior and/or exterior), such as office buildings and homes, for example, to provide higher energy efficiency, operation of components, and/or better security. A number of uses and methods of depth sensing VCA to monitor buildings are described below.

Occupancy Counting in Office Buildings

By analyzing whether a person is located in a particular part of an office building or room, lights can be controlled for those locations. For example, to optimize the use of lighting in office buildings for maximum energy efficiency, lights in unoccupied areas of an office building or home may be turned off (or dimmed, as per requirements) as soon as the areas become unoccupied or as soon as no motion is detected in the room (e.g., if a person in the room falls asleep). Similar controls can be applied to window blinds. The depth sensing features described herein, including use of depth to detect a head of a person, or use of depth to determine heights of detected objects, can be used to more accurately determine if a person is in a particular location.

In particular, in one embodiment, the lights in an office may be divided into zones that are slightly overlapping at their edges. Each zone may be controlled by one or more depth sensors depending on directionality requirements. The lighting control system can then be programmed per zone to turn on (brighten) lights when an object (e.g., a person) is detected within a certain radius around that zone, and turn them back off (dim) when there are no objects (e.g., people) within that radius.

In addition or instead of lighting management, heating and/or air conditioning may be controlled in response to the detection of whether a person is in a particular location. In addition, airflow and/or temperature settings of a thermostat for heating and/or air conditioning may be made based on a detection of a number of people in a building or in a particular location. For example, if only one person is detected to be present on a floor of a building (or no one is detected to be present in the building), lighting may be controlled to be on (or on in the location of the person), while airflow and/or temperatures for heating or air conditioning may be chosen to be more energy efficient. When one person or a certain number of people are detected to be present in the same location (for example, at least 5 or at least 10 or at least 20 people are present on a floor of a building, or at least one person occupies a smaller building, such as a house), airflow and/or temperatures for heating or air conditioning may be chosen more for comfort than for energy efficiency (e.g., airflow may be set higher when it is detected that the building location has a certain number of people present, a temperature for heating may be set to be higher when it is detected that the monitored building location has at least the certain number of people present and a temperature for cooling may be set to be lower when it is detected that the monitored building location has at least the certain number of people present). The building location may be monitored by video of images of the location with depth measurements, or may be monitored by video of images of the entrances and exits of the location with depth measurements (to track the number of people entering and exiting the building location, such as by using a video trip wire with depth information).

Counting people may also be used to control elevators of a building. Specifically, depth sensing VCA may be used to monitor a waiting area for one or more elevators. Floors having large numbers of people detected may be given higher priority or a higher weighting in deciding whether to stop at that floor. Depth sensing VCA may be used to detect the number of people in an elevator and use that detection to determine whether or not to stop at a floor to pick up additional people requesting an elevator or not. For example, when an elevator is at or near capacity, delivery of people within the elevator car may be given priority over (or a higher weighting) than stopping on a floor to accept waiting people waiting for the elevator, which may result in skipping floors even when people have requested an elevator. Use of depth sensing VCA may be particularly advantageous in these environments to accurately detect a number of people where image occlusion often may occur for reasons described elsewhere herein.

Determining Occupancy

The depth sensing VCA system can be used to better determine in a room the number of chairs that are occupied and that are vacant. This can be used to more accurately determine a person count in situations where audiences sit in chairs, and to better plan in real-time for occupancy-related issues. The chairs can be detected, in one embodiment, based on overall height (for example, using either maximum height or average height), and based on other attributes, such as shape, color, etc. The height of the chairs and the people (in chairs and/or standing) may be calculated from depth information associated with the images in the video. Comparing the detected height of the chair and the detected height of a person determined to be associated with the chair may be used to determine if the chair is occupied. If the detected heights of the chair and person associated with the chair are within a certain distance, it may be determined that the chair is occupied. Often the height of a chair and a seated person might be similar, but the combination of video and depth information may result in very accurate detection of whether the chair is occupied or not. Use of chair occupancy detection may result in actions to reduce power consumption. For example, when it is detected that all people in a room are seated in front of a TV, lights may be dimmed or turned off in the room. Chair occupancy (and/or people counting) may also be used to determine if a conference room is occupied. Alert of conference room occupancy may be appropriately sent out to a building manager or management system of the building. Conference room occupancy may be monitored to determine if the conference room is underutilized (unoccupied or occupied with smaller amounts of people than the conference room is designed to hold). Conference room occupancy can be used to determine parties who may abuse reservation of the conference room. When it is determined that the conference room is unoccupied during a time when the conference room has been reserved, the conference room reservation may be cancelled to allow others use of the conference room without needing to wait for the expiration of the reservation period.

Device Control within Buildings

Similarly, depth sensing VCA may be used to detect when a person goes to bed and when a person gets up from bed. Rather than chair occupancy, bed occupancy may be detected. Height information of the person may be determined from the depth information and video analysis and matched with expected height when the person is in bed. In addition, the person may be determined to be in a lying down that is not at floor level. And/or the person may be determined to be in a lying position coincident with the x,y coordinates of an object determined to be a bed. When a person is detected to go to bed, lights in the room may be turned off and/or blinds of windows may be closed. If it is determined that the house has no other people occupying it (or any other detected people are determined to be asleep), other energy saving measures may be performed, such as reducing a heating temperature of the house, or turning off other lights and/or electronic components in the house. When it is detected that the person has gotten up from bed, reverse actions may be performed, such as turning on lights, opening blinds, turning on a radio, etc.

Other lighting management can be performed using the disclosed embodiments. For example, people can be tracked in a room that includes a television, and if all people in the room are determined to be seated in front of the television (e.g., see exemplary details below regarding determining occupancy of a chair), then some or all lights in that room can be automatically turned off or dimmed. Chair occupancy may use the depth component with video content analysis to determine if a detected person and chair are aligned vertically and/or if the height of a person indicates a sitting height. This may be done by determining the x,y,z coordinates of a chair and a detected person that may qualify as an occupant (where overlap of x,y coordinates of the chair and the person may indicate occupation of the chair). Alternatively or in addition, the depth information of a chair and a person may be analyzed to determine if a difference in the corresponding depths is within a certain range.

In another embodiment, lights or an electronic device (e.g., projector, TV or stereo) can automatically turn on or off when a person waves an arm—for example, based on detected motion of a person but not detected motion of other objects. Arms may be more accurately detected with use of a depth component with video content analysis by determining an expected height of the arm and/or an expected positional relationship of an arm with respect to a head of the detected person. As noted, detection of people is made more accurate by use of depth (and derived height) information to detect head locations of people.

Depth sensing VCA is also be applicable to the following methods and systems:

Falling or Lying Down

In one embodiment, the depth sensing VCA system can be used to detect one or more people falling in a retail store. In addition to retail, detecting a human that has fallen down may be important, for example, in a healthcare a commercial environment. For example, the height of portions of a human (previously detected and classified as a human) may be reviewed to determine how close portions of the human is to the floor. For example, if the head within six inches of the floor and/or if a torso or a majority of a leg of a human is detected to be touching the ground, the human may be determined to have fallen down. A single person falling can be detected, and may be related to an emergency situation (e.g., a heart attack). As a result, an appropriate alarm can be activated. In addition, multiple people falling or lying down can be detected, which may correspond to a natural disaster or a human-caused catastrophe, such as an earthquake, bomb, attack, or other dangerous circumstance. For example, an abrupt change in height of a number of people at the same time may indicate that those people all fell to the ground at the same time and that some unusual event is occurring, which may trigger a notification (e.g., alarm) that review of the video or video environment (e.g., retail store) should be performed by management or emergency personnel. Furthermore, if those people then fail to get back up (e.g., height information continues to indicate they are on the ground), the system may determine that an event has occurred that requires assistance or further attention.

Adult Vs. Child Vs. Animal

In one embodiment, the depth sensing VCA system can be used to better count and differentiate objects in different groups. For example, the system can use height thresholds to differentiate between adults and children. This may be useful in retail environments to make more accurate correlations between sales and number of children present, or may be useful to determine which products attract greater attention by adults or children. In another embodiment, the system can be used in a home security environment to detect movement of objects in a person's home, but to filter out objects under a certain size, such as cats and small dogs.

Uses for Vehicles

The depth sensing VCA system can be used in various ways to improve analysis of vehicles. For example, it can be used to better count a number of vehicles in a store parking lot, or determine whether vehicles are speeding. The depth data can be calibrated to physical coordinates in the scene. Then, using the rate of change of depth for each vehicle tracked in the scene, the speed of the vehicle can be accurately calculated to determine whether it is speeding.

Another vehicle application is to monitor parking lots. By using a depth sensor, a surface model of one or more parking lot spaces may be created and monitored. A space emptiness measurement can be estimated to determine if each parking space is occupied. Data regarding which spaces are occupied and which are vacant can be stored and used by a central monitoring system, and can be used to keep track of parking lot capacity and availability in real-time.

In another embodiment, the depth sensing VCA system can be used to better count vehicles in general, such as for monitoring parking lot usage or traffic flow. The system may be programmed to monitor a line segment on parking lot or the road (e.g., across a road) and to monitor the depth of any objects at the line segment. When no vehicles are present, the depth of the road itself (i.e., an average distance between a depth sensor and the road surface at the designated line segment) may be determined, and a pulse, such as a binary "0" may be generated. When the detected depth of that segment changes (e.g., becomes greater than a threshold, as a result of a decreased distance between the sensor and a detected object at the designated line segment) for a period of time (which may be a short period of time required for a fast-moving vehicle to pass, or a longer period of time required for a slower-moving or longer vehicle to pass) the detected depth may indicate an object on the road for the period of time. As a result, a pulse, such as a binary "1" may be generated. The number of "1" pulses can then be recorded and used for vehicle flow analysis. In one embodiment, a camera and depth sensor are used that have a fast enough frequency (e.g., frames per second, or depth determinations per second) to accurately count vehicles moving up to a particular speed.

Depth information can also be used for vehicles to classify vehicle types at a given location. For example, different height thresholds can be set for cars versus trucks, or different widths can be set for cars versus motorcycles or bicycles. The depth information can also provide a three-dimensional volume measure instead of only a two-dimensional area measurement, which can more easily distinguish different types of vehicles.

Theft, Left Items

The depth sensing VCA system can be used to more accurately determine theft of items, or left items, in a setting. For example, a particular facility may have a certain set of items stored (e.g., a storage facility, store that is closed, etc.). The depth sensing VCA system can be used in a manner similar to vehicle flow monitoring, wherein a particular segment or area of a scene can be monitored, and an average depth of the area can be detected (e.g., an average distance between an image sensor and objects in the facility). If the average depth changes, for example if it decreases such that the average distance increases, the system can detect the difference in average distance, and may determine that an event, such as a potential theft has occurred. If the average depth increases such that the average distance decreases, the system can detect the difference in average distance, and may determine that an event, such as a potential item left behind has occurred. This can be used, for example, in airports, train stations, other transportation facilities or other public areas to monitor for suspicious items left where they are not supposed to be. In one embodiment, it can be used to detect rail theft of palettes removed from the system.

Odd/Suspicious Behavior

Security personnel are generally trained to look for certain behavior in people. Using the depth sensing VCA system, the system itself can recognize these behaviors and trigger alarms in response. For example, the system can look for erratic movements by monitoring fast changes in depth due to particular objects, or can better detect loitering using depth sensing. As another example, a camera sensor can recognize when a severe change in depth of an object has occurred, such as an event that coincides with a person covering the camera with an object to obscure the camera's view. Such an event can trigger an alarm.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present disclosure.

What is claimed is:

1. A method of monitoring a building comprising:
taking a video within a location in the building with a video sensor, the video comprising a plurality of frames, each frame including 2D image data;
for each frame, receiving depth data associated with the 2D image data, the depth data corresponding to one or more distances from the video sensor to features represented by the 2D image data;
analyzing the 2D image data including performing 2D analysis on the 2D image data to detect one or more image blobs in the video;
using the depth data, projecting an image blob of the one or more image blobs onto a plurality of Z-planes, thereby creating a plurality of blob slices;
separating the Z-planes into a ground plane and non-round planes based on a height threshold, so that at least a first blob slice on the ground plane is at or below the height threshold, and a second blob slice and additional blob slices on the non-ground planes are above the height threshold;
creating a refined blob that includes the second blob slice, the additional blob slices, and only a portion of the first blob slice;
performing object detection on the refined blob, to determine that the blob corresponds to a human object, thereby detecting a person in the video;

based on the detected person and one or more additional detected people, counting a number of people at the location in the building; and controlling a system of the building in response to the number of people counted.

2. The method of claim 1, wherein controlling a system comprises at least one of turning on lights and turning off lights of the building.

3. The method of claim 1, wherein controlling a system comprises setting a thermostat temperature of a heating system or a cooling system of the building.

4. The method of claim 1, further comprising providing an alert that at least one of a room or area is utilized when a number of people counted exceeds a predetermined value.

5. The method of claim 4, comprising providing an alert that a conference room of a building is utilized.

6. The method of claim 1, comprising counting a number of people that are sitting.

7. The method of claim 6, comprising detecting that people are sitting in front of a television, and reducing light usage of the building in response to detecting that people are sitting in front of a television.

8. The method of claim 1, further comprising detecting that a person has gone to bed.

9. The method of claim 8, further comprising detecting that a person has gone to bed by determining the person has lied down at a location other than the floor.

10. The method of claim 8, further comprising detecting that a person has gone to bed by detecting a height of the person.

11. The method of claim 8, further comprising reducing light usage of the building in response to detecting that the person has gone to bed.

12. The method of claim 8, further comprising controlling window blinds in response to detecting that the person has gone to bed.

13. The method of claim 1, further comprising detecting that a person has gotten out of bed.

14. The method of claim 13, further comprising, in response to detecting that a persona has gotten out of bed, controlling at least one of:
   lights of the building;
   window blinds;
   heating of the building; and
   cooling of the building.

15. The method of claim 1, further comprising:
   determining a number of people within an area near elevators by the analyzing the image data and the depth data;
   controlling elevator operation in response to the counting of the number of people.

16. The method of claim 15,
   wherein the depth data is used to determine heights of detected objects; and
   the determined heights of the detected objects are used to determine if the detected objects are people.

17. The method of claim 1, further comprising:
   determining a number of people within an elevator by the analyzing the image data and the depth data;
   controlling operation of the elevator in response to the counting of the number of people.

18. The method of claim 17,
   wherein the depth data is used to determine heights of detected objects; and
   the determined heights of the detected objects is are used to determine if the detected objects are people.

19. The method of claim 1, further comprising:
   determining an action of a detected person by analyzing depth data associated with the person;
   controlling a device within the building in response to the detected action.

20. The method of claim 19, wherein determining an action of the detected person comprises detecting that the person is waving an arm.

21. The method of claim 20, wherein controlling a device within the building in response to the detected action comprises controlling at least one of:
   light operation;
   projector operation; and
   blind operation.

22. The method of claim 1, further comprising:
   creating the refined blob by:
   determining a first region of the first blob slice that overlaps the second blob slice from a top down view; and
   including the first region of the first blob slice in the refined blob, without including a second region of the first blob slice in the refined blob.

23. The method of claim 22, wherein the second region of the first blob slice corresponds to a shadow or reflection.

24. A method of monitoring a building comprising:
   taking a video within a location in the building, the video comprising a plurality of frames, each frame including 2D image data;
   for each frame, receiving depth data associated with the 2D image data, the depth data corresponding to one or more distances from a depth sensor to features represented by the 2D image data;
   analyzing the 2D image data to detect at least a first image blob in the video;
   using the depth data, projecting the image blob onto a plurality of Z-planes, thereby creating a plurality of blob slices;
   based on a height threshold, separating the blob slices into a ground plane blob slice, and non-ground plane blob slices;
   creating a refined blob that includes non-ground plane blob slices, and only a portion of the ground plane blob slice;
   performing object detection on the refined blob, to determine that the blob corresponds to a human object, thereby detecting a person in the video; and
   controlling a system of the building in response to the detected person.

25. The method of claim 24, wherein the ground plane blob slice corresponds to a shadow or reflection.

26. The method of claim 24, further comprising:
   creating the refined blob by:
   determining a first region of the ground plane blob slice that overlaps the non-ground plane blob slices from a top down view; and
   including the first region of the ground plane blob slice in the refined blob, without including a second region of the ground plane blob slice in the refined blob.

* * * * *